(12) United States Patent
Koski

(10) Patent No.: US 11,833,010 B2
(45) Date of Patent: Dec. 5, 2023

(54) DEVICE AND METHOD FOR DENTAL PROCEDURE PLANNING

(71) Applicant: Robert Kyle Koski, Falls Church, VA (US)

(72) Inventor: Robert Kyle Koski, Falls Church, VA (US)

( * ) Notice: Subject to any disclaimer, the term of this patent is extended or adjusted under 35 U.S.C. 154(b) by 0 days.

(21) Appl. No.: 17/997,694

(22) PCT Filed: Dec. 22, 2021

(86) PCT No.: PCT/US2021/073089
§ 371 (c)(1),
(2) Date: Nov. 1, 2022

(87) PCT Pub. No.: WO2022/140791
PCT Pub. Date: Jun. 30, 2022

(65) Prior Publication Data
US 2023/0126119 A1 Apr. 27, 2023

Related U.S. Application Data

(60) Provisional application No. 63/264,691, filed on Nov. 30, 2021, provisional application No. 63/130,212, filed on Dec. 23, 2020.

(51) Int. Cl.
*A61C 8/00* (2006.01)
*A61B 6/14* (2006.01)
*A61C 9/00* (2006.01)

(52) U.S. Cl.
CPC .............. *A61C 8/009* (2013.01); *A61B 6/145* (2013.01); *A61C 9/0046* (2013.01)

(58) Field of Classification Search
CPC ........ A61C 8/009; A61C 9/0046; A61B 6/145
USPC .......................................................... 433/214
See application file for complete search history.

(56) References Cited

U.S. PATENT DOCUMENTS

| | | |
|---|---|---|
| 7,758,345 B1 | 7/2010 | Christensen |
| 8,750,590 B2 | 6/2014 | Greenberg |
| 8,805,658 B2 | 8/2014 | Pettersson et al. |
| 9,750,582 B1 | 9/2017 | Buchanan |

(Continued)

FOREIGN PATENT DOCUMENTS

| | | |
|---|---|---|
| KR | 101152851 B1 | 6/2012 |
| KR | 101452718 B1 | 10/2014 |

(Continued)

OTHER PUBLICATIONS

Balasundaram, A. et al. "Novel CBCT and Optical Scanner-Based Implant Treatment Planning Using a Stereolithographic Surgical Guide: A Multipronged Diagnostic Approach" *Implant Dentistry*, Aug. 2014, 23(4):401-406.

(Continued)

*Primary Examiner* — Matthew M Nelson
(74) *Attorney, Agent, or Firm* — SALIWANCHIK, LLOYD & EISENSCHENK

(57) ABSTRACT

The invention concerns a device for obtaining an occlusal registration of a patient; a method for obtaining an occlusal registration of a patient; and a method for dental procedure planning, such as dental implant planning. Radiopaque markers are advantageously applied to improve the devices, methods, and outcomes related to dental procedures.

6 Claims, 14 Drawing Sheets

121 – shape of known dimension
122 – radiopaque fiducial marker
123 – interior surface facing device
124 – body
125 – exterior surface facing patient

(56) References Cited

U.S. PATENT DOCUMENTS

| | | | |
|---|---|---|---|
| 10,136,970 B2* | 11/2018 | Pesach | A61C 9/006 |
| 10,206,757 B2 | 2/2019 | Pettersson | |
| 11,020,208 B2* | 6/2021 | Pesach | A61B 5/0088 |
| 2004/0011976 A1 | 1/2004 | Kay | |
| 2009/0063192 A1 | 3/2009 | Giles | |
| 2009/0220134 A1* | 9/2009 | Cahill | B33Y 50/00 |
| | | | 382/128 |
| 2009/0291416 A1* | 11/2009 | Brunson | A61C 9/006 |
| | | | 433/215 |
| 2012/0123576 A1* | 5/2012 | Pettersson | A61C 9/004 |
| | | | 700/98 |
| 2012/0191421 A1 | 7/2012 | Greenberg | |
| 2012/0230567 A1 | 9/2012 | Greenberg | |
| 2013/0337400 A1 | 12/2013 | Yi et al. | |
| 2014/0180065 A1 | 6/2014 | Garcia | |
| 2014/0270067 A1* | 9/2014 | Clark | A61B 50/30 |
| | | | 378/163 |
| 2015/0196372 A1* | 7/2015 | Champleboux | A61C 9/0046 |
| | | | 433/29 |
| 2015/0348320 A1* | 12/2015 | Pesach | A61C 9/006 |
| | | | 382/128 |
| 2016/0235483 A1* | 8/2016 | Zeilhofer | A61B 34/20 |
| 2017/0312065 A1* | 11/2017 | Marshall | A61B 5/0077 |
| 2018/0303583 A1* | 10/2018 | Tong | A61C 7/146 |
| 2019/0151046 A1* | 5/2019 | Kim | A61B 6/032 |
| 2019/0380811 A1* | 12/2019 | Kim | A61C 1/084 |
| 2020/0146790 A1* | 5/2020 | Marshall | A61B 5/0088 |
| 2021/0192759 A1* | 6/2021 | Lang | G06T 3/40 |
| 2022/0079533 A1* | 3/2022 | Bell | A61B 90/39 |
| 2022/0087791 A1 | 3/2022 | Choi et al. | |

FOREIGN PATENT DOCUMENTS

| | | |
|---|---|---|
| WO | WO 2012150843 A2 | 11/2012 |
| WO | WO 2020171314 A1 | 8/2020 |

OTHER PUBLICATIONS

Jones and Dalmau "Clinical Case Report: iTero® Digital Scanning Technology and Tooth-Supported Surgical Guides" Nov. 4, 2013, retrieved on Oct. 22. 2020 from https://glidewelldental.com/education/inclusive-dental-implant-magazine/volume-4-issue-2/clinical-case-report-itero-digital-scanning-technology-and-tooth-suppertedsurgical-guides/ (15 pages).

* cited by examiner

Markers

Side view

Top view

1 – occlusal registration material
2 – radiopaque fiducial markers

Device in use

Exploded view

1 - occlusal registration material
2 - radiopaque fiducial markers

Side view

Top view

1 — occlusal registration material
2 — radiopaque fiducial markers

1 – occlusal registration material
2 – radiopaque fiducial markers
3 – cotton roll or other separator Markers Markers Surgical guide Top view 1 — occlusal registration material
2 — radiopaque fiducial markers Side view 121 — shape of known dimension
122 — radiopaque fiducial marker
123 — interior surface facing device
124 — body
125 — exterior surface facing patient Side view of device
in mouth of patient

DEVICE AND METHOD FOR DENTAL PROCEDURE PLANNING

CROSS-REFERENCE TO RELATED APPLICATIONS

The present application is the National Stage of International Application Number PCT/US2021/073089, filed Dec. 22, 2021, and claims the benefit of U.S. Provisional Application Ser. No. 63/264,691, filed Nov. 30, 2021, and U.S. Provisional Application Ser. No. 63/130,212, filed Dec. 23, 2020, each of which is hereby incorporated by reference herein in its entirety, including any figures, tables, nucleic acid sequences, amino acid sequences, or drawings.

BACKGROUND OF THE INVENTION

Dental implants are a highly desirable option for patients seeking to replace missing teeth. In recent years, several advancements have been made in the field of implant dentistry that has made the dental implant procedure safer, more efficient, and more successful. One of the breakthrough advancements in implant and surgical dentistry is digital planning.

Dentists are using digital scanners to create models of patients' dentition in conjunction with or in place of physical casts or impressions. The digital models created from these scans are being utilized to plan dental implant and other surgical and dental procedures; however, there is not currently a sufficiently robust, timely, and convenient method to precisely align the digital image of the patient's dentition with the cone beam computed tomography (CBCT) image of the patient. Alignment imprecision could lead to errors in surgery or other unforeseen consequences.

Conventional method for dental implant planning can require that the patient attend two appointments, as summarized by the flow chart of FIG. 2. The first appointment can include an evaluation. At this appointment a dental examination can be conducted to determine the suitability of the patient to receive a dental implant. Several factors can be considered: the patient's medical and dental history, an evaluation of the site of the missing tooth or teeth, and an assessment of the patient's overall dental health and hygiene. Dental impressions (digital and/or physical) can be captured at this first appointment to create an accurate model of the patient's teeth for study.

The positive reproduction of a patient's teeth and associated soft tissue made from a dental impression obtained from the patient either physically or digitally, is a type of dental model that may be referred to as a "study model", "study cast", or "diagnostic cast" and is an important component in dental implant planning. The study model is a physical (e.g., stone cast or negative impression) or digital replica of the patient's hard and soft tissues that allows study of the dentition outside the patient's mouth. The study model is often a highly accurate model that can be used to fabricate dental appliances. In dental implant planning, the study model can be used to make a radiographic guide and a surgical guide. The radiographic guide and surgical guide can be fabricated separately by the dental laboratory or in office by the dentist after the first appointment and second appointment, respectively.

The radiographic guide, also known as a scan appliance, is an oral appliance that fits over the patient's teeth much like a retainer and can contain radiopaque markers that are discrete from (e.g., adjacent to) the teeth of the patient and are discernible on x-rays and cone beam computed tomography (CBCT) scans. The radiographic guide is an important appliance because it allows the dentist to capture discrete, repeatable points related to the teeth that can be used to plan precisely where the implant should be placed in that patient's mouth. If a patient has a large number of restorations, the CBCT image can be difficult or impossible to interpret without these discrete points to guide the dentist. The radiographic guide can also speed up the planning process.

The scan appliance is typically used at the second appointment. The patient returns to the clinic after fabrication of the scan appliance, and a CBCT scan is made of the patient as they wear the scan appliance. The CBCT scan produces a 3-dimensional image of the patient's dentition with known, reproducible markers discrete from (e.g., adjacent to) the teeth. A CBCT image of the study cast is then captured with the same scan appliance in place on the cast. Another method of generating a study cast is a digital scan of the patient's dentition. A digital scanner using optical or other digital means of capture takes images of the patients mouth and software generates a three-dimensional study model of the images. There can be challenges in merging the digital image from the scanner with the CBCT image. This process produces two 3-dimensional, digital images: one of the patient's mouth and one of the study cast. Each image has the radiopaque markers in precisely the same relative location because the radiographic guide fits in relatively the same manner with a high degree of precision on both the patient and the study cast.

The dentist and the dental laboratory typically coordinate to merge the two images using an implant planning software program. Merging the images allows the dentist to plan the implant surgery with a high degree of accuracy on the image of the patient and then translate that plan to the image of the study cast so that a surgical guide can be made from the study cast. The radiographic markers being in the same location discrete from (e.g., adjacent to) the teeth on the cast and patient allows a sufficiently accurate merge of the two images. This high degree of accuracy in planning greatly improves surgical success and efficiency. Optionally, a digital rendering can be made of the study model using an optical scanner, to produce a digital study model, and the digital study model can also be merged with the two CBCT images.

Once the plan is completed, the dental laboratory fabricates a surgical guide from the implant planning software. The surgical guide is used by the surgeon to place the implant in the precise location where it was planned, relative to the patient's teeth. This gives the implant the best chance for success by helping the surgeon plan to avoid weak areas in bone, anatomical landmarks like nerves and blood vessels, and maximize the amount of stable bone and soft tissue supporting the implant. Surgical guides have dramatically improved outcomes of implants while decreasing surgical placement time but with costs including additional appointments, expenses, processing time, and complexity.

Efficiency and speed are highly beneficial to the successful practice of dentistry. Eliminating unnecessary appointments or reducing time spent on a procedure would allow dentists to treat more patients, and increase revenue, while improving patient outcomes.

BRIEF SUMMARY OF THE INVENTION

The present invention provides a dental occlusal (i.e., bite) registration device; methods for obtaining an occlusal registration using the device; and methods for dental procedure planning, such as dental implant planning, using the device. The devices and methods of the invention are advantageous in consolidating patient chair time to one appointment and reducing expenditure of dentist office resources and laboratory resources spent in cases where a laboratory is used for the dental procedure planning process.

When a patient goes to the dentist in need of any planned dental procedure, for example a dental implant, both the dentist and patient desire predictable and successful outcomes; therefore, the dentist can create a surgical guide to ensure highly accurate implant placement. While related art methods can require at least two appointments or additional chair time to create a surgical guide and complete procedure planning (adding time, cost, and complexity) the device and methods of the invention can reduce procedure planning to one appointment and deliver a surgical guide more rapidly and with less expense. Embodiments can be used, for example, to capture an occlusal registration or to capture a full or partial registration of just one arch of the teeth. In certain embodiments found throughout this disclosure the occlusal registration can be full or partial, and can include both or either arch.

One embodiment of the invention provides a device for obtaining an occlusal registration or other dental registration, record, or impression of a patient, comprising:

a base portion comprising occlusal registration material and arranged for fitting into the mouth a patient, wherein the base portion has opposing upper and lower contacting surfaces configured to be imprinted with, and maintain an impression of, the patient's dentition in the occlusal registration material;

a plurality of radiopaque fiducial markers arranged in fixed positions within the base portion, between the upper and lower contacting surfaces, wherein the fixed positions of the radiopaque fiducial markers provide reference points to determine specific anatomical areas of dentition when the base portion is fitted into the mouth of the patient and radiographically imaged. The occlusal registration device can be useful for obtaining occlusal registrations for dental procedure planning, such as dental implant planning. The fiducial markers are arranged within the body portion of the device to remain out of contact with the patient's teeth when the patient bites on the device for occlusal registration.

Another embodiment provides a method for obtaining an occlusal registration of a patient, comprising placing a device of the invention into the mouth of the patient, wherein the patient's occlusal registration can be obtained when the patient bites on the upper and lower contacting surfaces, making an impression of the patient's dentition in the occlusal registration material. The occlusal registration is useful for dental procedure planning, such as dental implant planning.

Another embodiment provides a method for dental procedure planning, such as dental implant planning, comprising:

(a) obtaining an occlusal registration of a patient by placing a device in accordance with the subject invention into the mouth of the patient, wherein the patient's occlusal registration is obtained when the patient bites on the contacting surfaces of the device, making an impression of the patient's dentition in the occlusal registration material; and (b) obtaining a digital three-dimensional radiographic image of the patient's mouth with the device placed in the patient's mouth.

Further steps can be carried out before, during, or after (a) and (b), as described in more detail herein.

BRIEF DESCRIPTION OF THE DRAWINGS

FIG. 1A shows an embodiment of the base portion of the device. FIG. 1B shows the base portion of the device with radiopaque fiducial markers indicated ("markers"). FIG. 1C is a top view of a first embodiment of the device, with the base portion composed of occlusal registration material (1), and radiopaque fiducial markers (2) indicated. FIG. 1D is a side view of the first embodiment of the device, showing the base portion composed of occlusal registration material (1), and radiopaque fiducial markers (2) indicated. FIG. 1E is an exploded view of the first embodiment of the device, showing radiopaque fiducial markers (2) each in a separate vertical plane (represented by vertical lines in this figure) arranged between two adjacent layers of occlusal registration material (1). FIG. 1F is a side view of the first embodiment of the device in use in a patient's mouth, between the patient's upper and lower rows of teeth, with the occlusal registration material (1) and radiopaque fiducial markers (2) indicated. FIG. 1G is a top view of a second embodiment of the device, with the base portion composed of thicker (as compared to the first embodiment) layers of occlusal registration material (1), and radiopaque fiducial markers (2) indicated in a non-planar constellation. FIG. 1H is a side view of the second embodiment of the device, showing the base portion composed of occlusal registration material (1), and radiopaque fiducial markers (2) indicated. FIG. 1I is an exploded view of the second embodiment of the device, showing radiopaque fiducial markers (2) each in a separate vertical plane (represented by vertical lines in this figure) arranged between two adjacent (and thicker, as compared to the first embodiment) layers of occlusal registration material (1). FIG. 1J is a side view of the second embodiment of the device in use in a patient's mouth, between the patient's upper and lower rows of teeth, with the occlusal registration material (1) and radiopaque fiducial markers (2) indicated. The upper panel of FIG. 1J shows the device registering both upper and lower teeth of the patient by direct engagement with the same occlusal registration material. The lower panel of FIG. 1J shows the device registering the lower teeth of the patient by direct engagement with the occlusal registration material while the upper teeth are engaged by a spacer material (3).

DETAILED DESCRIPTION OF THE INVENTION

Embodiments of the subject invention provide devices, systems, and methods for determining or recording information pertaining to the structure, position, and relationships between one or more teeth in the mouth of a patient. Certain embodiments are configured to obtain a complete static occlusal registration. Certain embodiments are configured to obtain an imprint, scan, or digital representation of one arch of the teeth of a patient. Alternative embodiments are configured to obtain an imprint, scan, or digital representation of one or more teeth. Embodiments provide devices, systems, and methods to advantageously align and register different representations (e.g., one or more of a negative impression, casting, mold, image, visual scan, x-ray, magnetic resonance imaging (MRI), tomography, or other physical, analog, or digital representation of physical structures such as teeth, bones, or soft tissues of the mouth, jaw, nasal cavity, or surrounding tissues.) While individual examples and discussions throughout this disclosure may focus on a specific procedure or area of application (e.g., occlusal registration useful for planning an implant and related procedures) it should be appreciated that invention is not limited to only these exemplified embodiments.

In one embodiment, the subject invention provides a device for obtaining an occlusal registration of a patient, comprising:

a base portion comprising occlusal registration material and arranged for fitting into the mouth a patient, wherein the base portion has opposing upper and lower contacting surfaces configured to be imprinted with, and maintain an impression of, the patient's dentition in the occlusal registration material;

a plurality of radiopaque fiducial markers arranged in fixed positions within the base portion, between the upper and lower contacting surfaces, wherein the fixed positions of the radiopaque fiducial markers provide reference points to determine specific anatomical areas of dentition when the base portion is fitted into the mouth of the patient and radiographically imaged. The occlusal registration device is useful for obtaining occlusal registrations for dental procedure planning, such as dental implant planning.

Figure 1A:
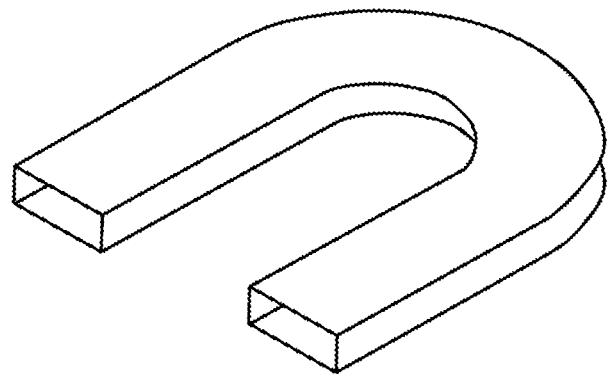
FIGS. 1A-1J show embodiments of an occlusal registration device of the invention.
Figure 1B:
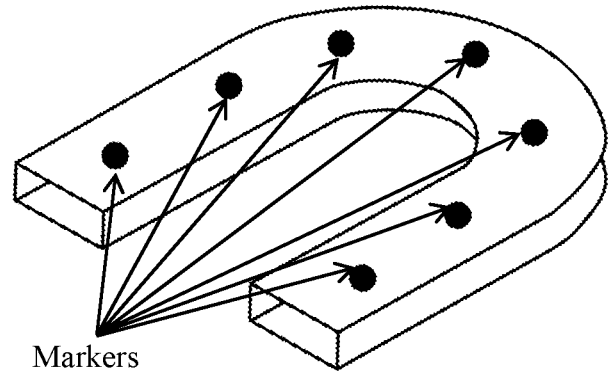
Figure 1D:
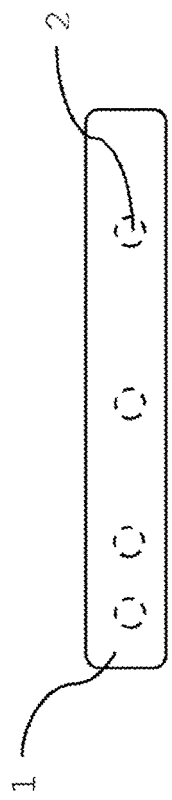
Figure 1C:
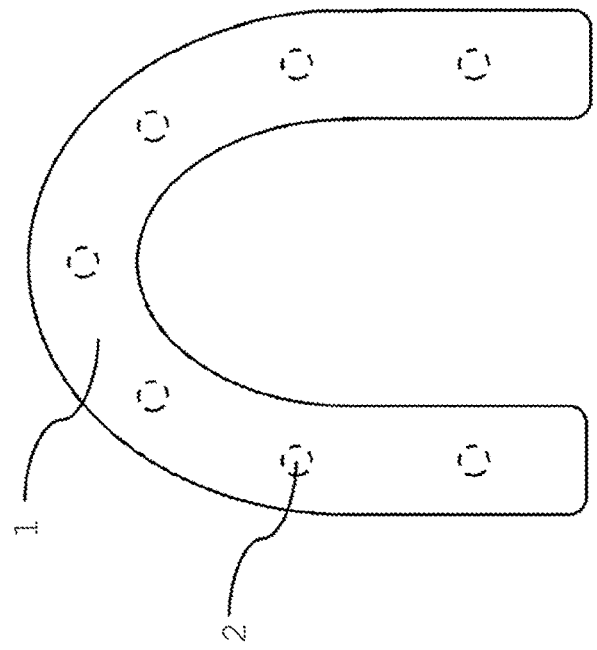
Figure 1F:
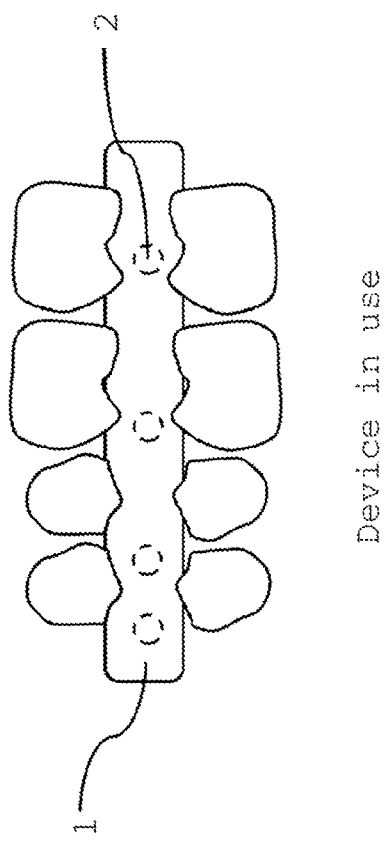
Figure 1E:
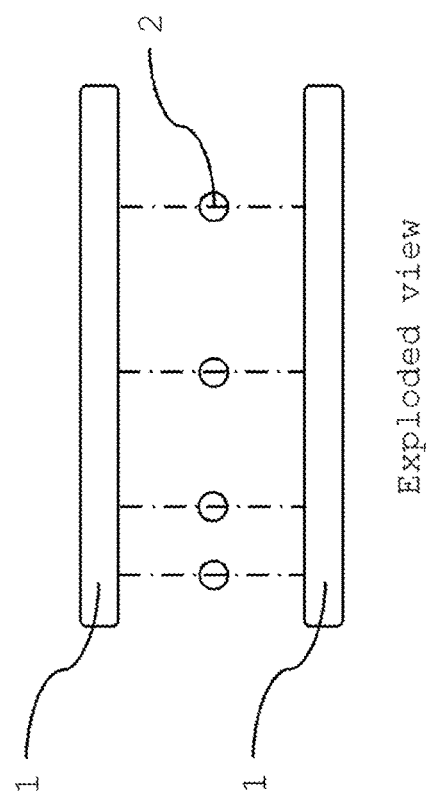
Figure 1H:
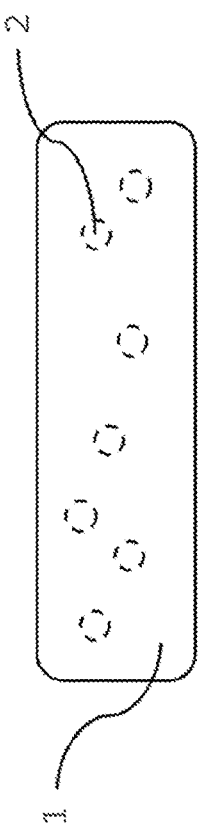
Figure 1G:
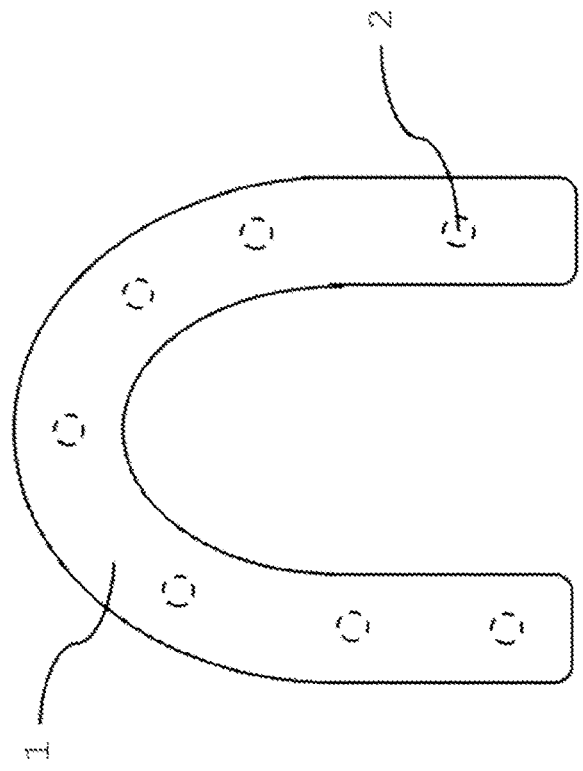
Figure 1I:
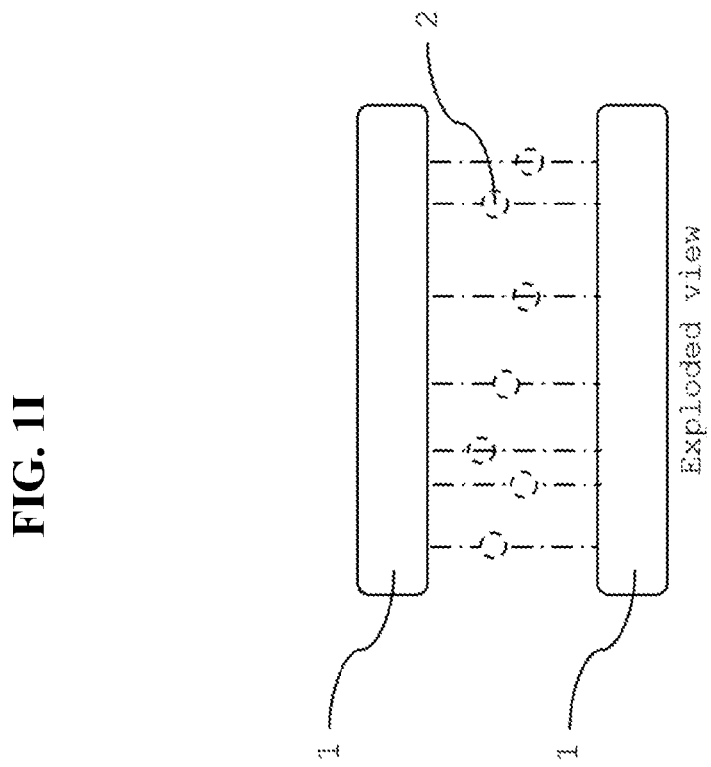
Figure 1J:
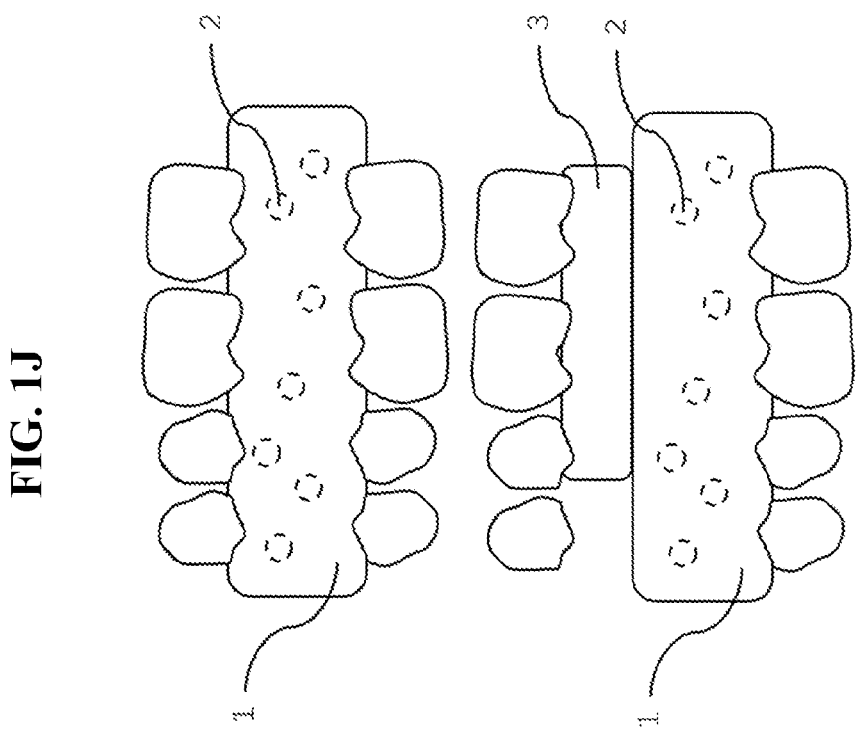
Figure 2:
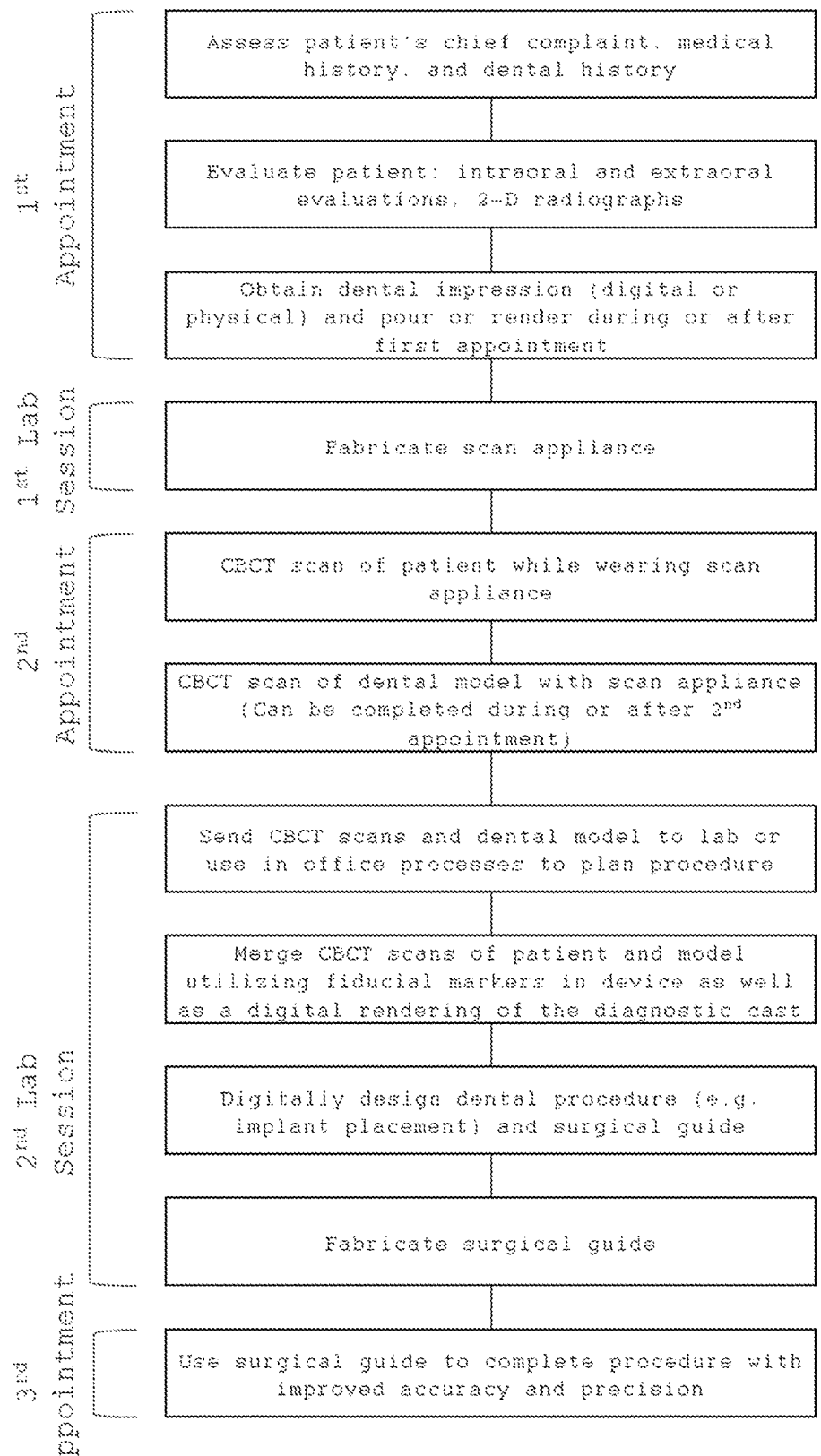
FIG. 2 is a flow chart summarizing a related art method for dental procedure planning, which includes a first patient visit, fabrication of a scan appliance, and a second planning appointment to take CBCT scans of both the patient wearing the scan appliance and the dental model fitted with the scan appliance.

In some embodiments, the base portion has a laminated structure with two or more adjacent layers of occlusal registration material, and the plurality of radiopaque fiducial markers are arranged in fixed positions between the adjacent layers, as shown representatively by FIG. 1E. Producing the device as a laminate beneficially ensures that each of the markers is placed in a known fixed position (e.g., at a predetermined depth) within the base portion of the device.

Embodiments can have additional layers and additional materials, as can be required or beneficial for each application. Additional layers can, for instance, further protect the fiducial markers, add radiopacity, stabilize the device, help handling (e.g., by providing a handling tab integrated into the layer), or include other types of material.

The occlusal registration material in certain embodiments is selected to be sufficiently thermoplastic to allow accurate capture of the patient's teeth (or arch, or bite), but sufficiently temperature stable so that it will not distort outside the patient's mouth. In some embodiments, the occlusal registration material is occlusal wax. However, other suitable occlusal registration materials can include acrylic, vinyl polysiloxane, silicone, polyether, zinc oxide eugenol, or any combination of two or more of the foregoing. Wax can be chosen in certain embodiments for advantages including low price, high availability, and high usability. Multiple layers can be provided (e.g., to further stabilize the markers). Plastic or other radiolucent material can be used in combination in the layering of certain embodiments for advantages including improved structure or support.

Embodiments provide an occlusal registration device as opposed to a dental impression tray, which uses impression material. Certain embodiments provide a base composed of the same material throughout (i.e., homogeneous material composition.) Advantageously, a homogenous base in accordance with certain embodiments can be less expensive to manufacture, and more easily used than an impression tray or other related devices.

Certain embodiments provide an upper and lower occlusal registration where the patient bites into the top and bottom surfaces simultaneously. Alternative embodiments provide either an upper biting surface, a lower biting surface, or both. In certain embodiments a patient can bite on both top and bottom surfaces at the same time, bite on one surface and then the other, bite on one surface at a time, or bite on only one surface. If biting on one surface, the patient can be provided a cotton roll or other stabilizing implement to stabilize the device while scans are being obtained.

In certain embodiments the fiducial markers can be composed of any radiopaque material or materials that will be discernible on the three-dimensional radiographic imaging modality to be utilized (e.g., computed tomography (CT) or cone beam computed tomography (CBCT)). For example, the radiopaque material can include gutta percha, barium sulfate, silicon carbide, silicon nitride, aluminum oxide, non-eugenol temporary dental cement (e.g., a non-eugenol temporary dental cement such as TempBond™ NE cement, available from KERR CORPORATION, Brea, CA), metals that are safe to the patient, restorative dental cements, or any combination of two or more of the foregoing. The radiopaque material can be solid, or can be semi-solid, or liquid so long as the markers will remain in a known, fixed position within the device for use to perform their fiducial function.

The plurality of radiopaque fiducial markers can be of a shape and quantity, and arranged within the device, so as to provide the necessary anatomical information of the patient's mouth in the three-dimensional radiographic imaging for procedure planning. The markers can be sufficiently discrete in form (e.g., having discrete margins or boundaries) and have a configuration to provide the necessary anatomical formation of the patient's mouth. In some embodiments, the markers are spherical in shape. In some embodiments, the plurality of markers includes three or at least three markers. In other embodiments, the plurality of markers is five to seven markers.

In certain embodiments, three or more markers can be useful for proper triangulation or orientation. Spacing can be arranged so markers do not overlap or interfere on scans such as CBCT. Placement of markers can be in different planes. Markers can be provided in any size large enough for scanning technology (e.g., CBCT) to capture and small enough for patient comfort and fit. Markers can be provided in spherical, cylindrical, polygonal, and specific shapes of known geometry or dimension. Markers can be advantageously provided with specific dimensions to benefit both dentist and patient. In some embodiments, markers can be provided having a diameter, width, height, length, thickness, or other useful largest, average, median, nominal, or smallest dimension of 0.1 mm, 0.5 mm, 1 mm, 1.5 mm, 2 mm, 2.5 mm, 3 mm, 4 mm, 5 mm, or more than 5 mm, including ranges, increments, divisions, combinations, and multiples thereof, as determined by the available imaging technology, needs of the patient, and needs of the dentist. In an embodiment, spherical markers of about 2 mm diameter are provided. In an alternative embodiment, markers comprising one or more shapes of known dimension having a height of less than 2 mm, a length of more than 2 mm, and a thickness of less than 1 mm are provided. In another alternative embodiment, markers comprising one or more shapes of known dimension having a height of about 2 mm, a length of about 10 mm, and a thickness of about 0.5 mm are provided. Markers can be provided with a single consistent shape and size, or with one or more markers of different shapes or different sizes within a single device, or across multiple devices.

In some embodiments the markers do not extend beyond the outer surfaces of the device and should be of sufficient depth within the base portion of the device to remain out of contact with the patient's teeth when the patient bites on the device for occlusal registration, as shown representatively by FIG. 1F. An internal arrangement of markers can advantageously avoid damage or displacement of the fiducial markers by the patient's teeth, as well as avoiding discomfort, pain, or damage to the patient from contact with the markers. In other embodiments, markers can advantageously approach, approximate, touch, follow, define, cross, extend beyond, or protrude from one or more outer surfaces of the device. As a non-limiting example, a cylindrical marker can be provided in a position extending laterally from the device to provide a registration point, manufacturing aid, or guidance point for producing, handling, inserting, removing, registering or aligning the device either in or out of the mouth of the patient. As another non-limiting alternative example, a marker can be provided as a registration or contact point intended to approximate, align with, or contact a tooth or other anatomical landmark of the patient or a piece of surgical apparatus.

The base portion of the device can be any shape or configuration that is conducive to providing the necessary anatomical information of the patient's mouth in the three-dimensional radiographic imaging for procedure planning. In some embodiments, the base portion is configured as a planar sheet having a rectangular, nearly rectangular, rounded, oval, or oblong shape. In some embodiments, the base portion has a generally U-shape when viewed from the top or bottom, or horseshoe configuration (e.g., following the occlusal arch), as shown in FIGS. 1A-1C. The shape of the base portion (e.g., those shapes mentioned above) can be chosen to provide benefits including comfort, manufacturing ease, and optimization of material cost.

Optionally, the base portion of the device further includes a tab for handling the device during insertion, adjustment, and/or removal from the patient's mouth, in which the tab can extend out of the patient's mouth when the device is placed in the patient's mouth. The tab can be flexible or rigid, and can be integral with the base portion or attached thereto. The tab can be composed of the same material (e.g., occlusal registration material) as other areas of the device, or be of a different material (e.g., not necessarily occlusal registration material). The tab should be large enough or configured to grasp in order to place and remove appropriately, either by hand, with common instrumentation, or with specialized instrumentation.

Certain embodiments can provide part of a kit that includes one or more additional components useful for carrying out the dental planning procedure (e.g., dental implant planning procedure), such as one or more implant components (e.g., implant body, abutment) and/or implant placement components (e.g., bone taps, twist drills). The kit can include one or more of the following components: tubes for guiding instruments through a surgical guide, implant mounts used to position the tubes in the surgical guide or to place implants, tissue punches to be used through the tubes, drill position handles, twist drills, bone taps, bone profilers to manually remove crestal bone for proper abutment seating after implant placement, and various instruments such as drivers and ratchets to place implants. The kit can include one or more components for endodontic surgeries, such as apical pluggers and filling instruments. The kit can include packaging for one or more components, and optionally include printed and/or digital instructions for their use. The kit can be used for carrying out the methods of the invention, or for other uses.

An embodiment can provide a method for obtaining an occlusal registration of a patient, comprising placing a device according to an embodiment of the subject invention into the mouth of the patient, wherein the patient's occlusal registration is obtained when the patient bites on the upper and lower contacting surfaces, making an impression of the patient's dentition in the occlusal registration material. The occlusal registration is useful for dental procedure planning, such as dental implant planning.

An embodiment can provide a method for dental procedure planning, such as dental implant planning, comprising:

(a) obtaining an occlusal registration or registration of the desired arch of teeth or individual teeth or tooth of a patient by placing a device according to an embodiment of the subject invention into the mouth of the patient, wherein the patient's occlusal registration is obtained when the patient bites on one or more of the upper or lower contacting surfaces of the device, making an impression of the patient's dentition in the occlusal registration material; and (b) obtaining a digital three-dimensional radiographic image of the patient's mouth with the device placed in the patient's mouth.

A physical or digital impression is obtained of the patient's dentition. If an optical scan or digital rendering of the patient's dentition is used (e.g., OmniCam), a shape of known dimension can be used to determine the precise location of the connected fiducial markers relative to the patient's dentition. If the physical impression is obtained, a cast or digital rendering can be made. A CBCT scan can also be made of the physical cast with the scan appliance.

Further steps of the dental procedure planning method can be carried out before, during, or after (a) and (b), as described in more detail below, and exemplified by the flow chart of FIG. 3. It will be understood that in certain embodiments (b) can be performed before or after other steps including (c), as described below.

Optionally, prior to obtaining the occlusal registration of the patient in (a), the planning method further includes assessing the patient's complaint, medical history and dental history.

The devices and methods of certain embodiments of the invention can be used for planning a variety of dental procedures, including planning any dental implant procedure. For example, the dental implant can be endosteal or subperiosteal, and the implant procedure can include one or more adjunctive procedures such as bone augmentation, sinus lift, and ridge expansion if needed. Dental implants can be made of various materials, such as titanium, zirconia, gold, stainless steel, or cobalt-chromium.

In addition to dental implant procedures, the devices and methods of the invention can be used for planning dental procedures such including orthodontic treatments (e.g., braces), endodontic procedures (e.g., root canals, apical surgeries), periodontic procedures (e.g., bone grafting, sinus lift), and prosthodontic applications (e.g., making partial dentures).

In some embodiments of the planning method, the method further includes: (c) obtaining a digital three-dimensional radiographic image of a dental model of the patient with a device according to the subject invention placed on the model. In some embodiments of the planning method, the method further includes: (d) merging (e.g., digitally, visually, graphically, or physically aligning data from two or more different sources) the radiographic image of the patient's mouth and the radiographic image of the dental model utilizing the radiopaque fiducial markers; or providing the radiographic image of the patient's mouth and the CBCT scan of the dental model to a laboratory to perform the merging.

In certain embodiments, optical imaging is supported by using the shape of known dimension to align visual and radiographic scans. In other embodiments two or more CBCT scans are used to capture both the patient with scan appliance and the cast with scan appliance for merging.

Related art can require two office visits wherein a conventional scan appliance is fabricated by a dental laboratory using the physical dental cast taken at the first visit and then applied for patient imaging at the second visit. Even if a digital impression is used to make a scan appliance, it is typically sent to a lab for fabrication. This takes time and while it can be done same-day or in-office, it often is not for reasons including at least cost, capacity, and capabilities of the service provider to fabricate the appliance. The patient returns to the clinic for the second appointment after the scan appliance is fabricated. The subject invention allows one step because it provides a scan appliance that can be accurately related to the teeth without laboratory fabrication. The scan appliance of the subject invention provides a stable apparatus for the radiographic markers to custom fit to a patient.

Many specific problems are solved by embodiments of the subject invention. To begin with, certain embodiments are far less expensive than available alternatives. A traditional scan appliance can cost $75 or more. Embodiments can cost $5, or less. Second, the subject invention eliminates an additional appointment by consolidating appointments 1 & 2. The patient can have a CBCT scan the same day that they come in for implant planning. This saves time and money for the patient and provider. With the SKDs provided in certain iterations, this invention also allows digital scans to be readily incorporated in dental procedure planning because it eliminates additional laboratory fabrication of scan appliances and models of the digital rendering.

Figure 3:
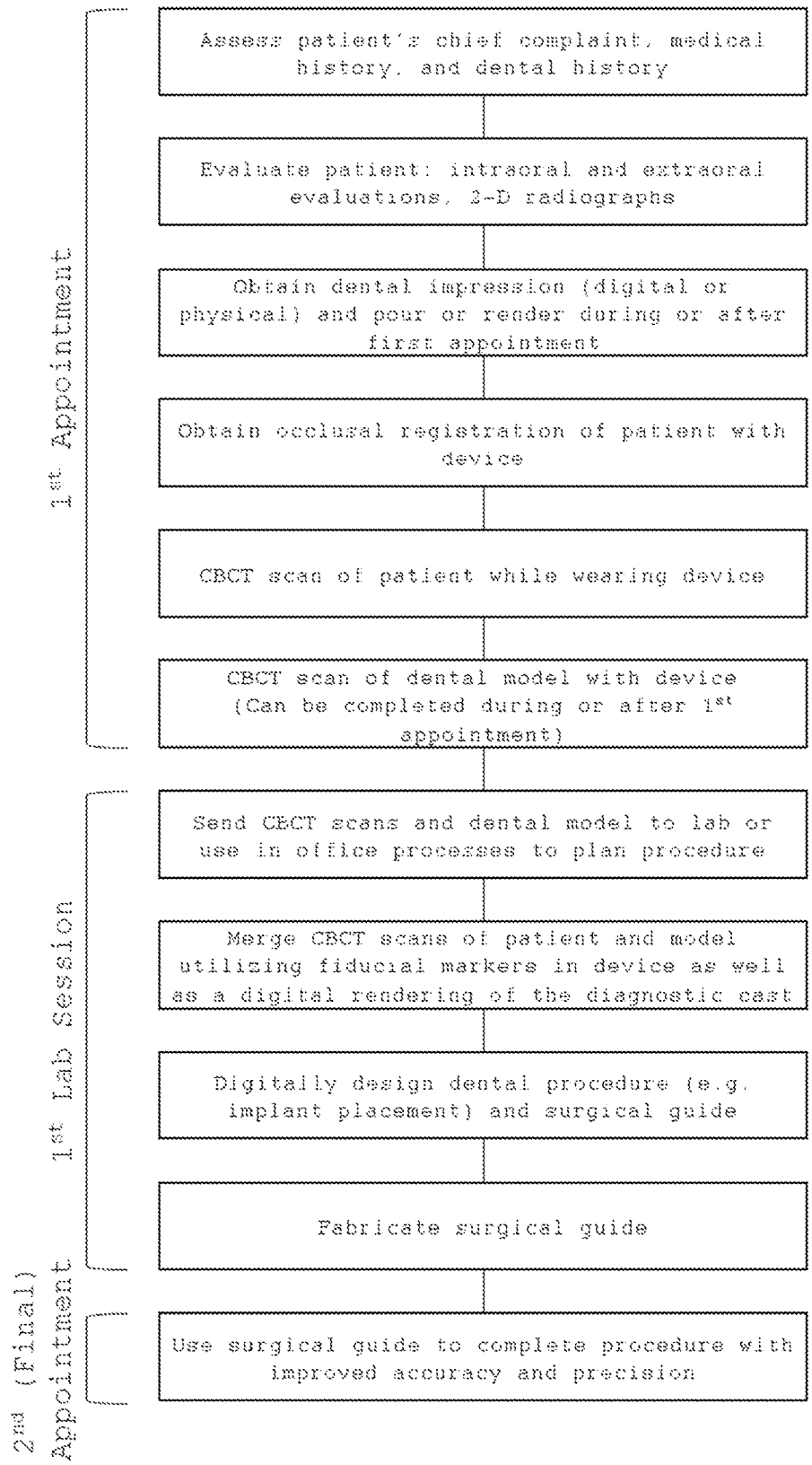
FIG. 3 is a flow chart summarizing a method for dental procedure planning according to an embodiment of the subject invention, showing procedure planning reduced to a single appointment by advantageous application of a device according to an embodiment of the subject invention.

Optionally, a digital rendering can also be made of the diagnostic cast or the patient, to produce a digital study model, and the digital study model can also be merged with the two radiographic images (e.g., merging all three images, or merging each pair of two images in parallel), as indicated in FIG. 3. The digital rendering of the diagnostic cast can be made using an optical scanner, such as the inLab inEos X5 Scanner (Dentsply Sirona, Charlotte, NC, USA). Optical scanners scan diagnostic casts and impressions to render digital models of a patient's dentition. Intraoral scanners such as the CEREC OmniCam scanner (Dentsply Sirona, Charlotte, NC, USA) can be used chairside to obtain a diagnostic impression of the patient. This file can then be used in the procedure planning and combined with radiographic or other images of the patient.

In certain embodiments, optical imaging is supported by using a shape of known dimension provided on a scan appliance in accordance with an embodiment of the subject invention to align visual and radiographic scans. In other embodiments two or more CBCT scans are used to capture both the patient with scan appliance and the cast with scan appliance for merging.

Merging software such as BlueSkyBio (Blue Sky Bio, LLC, Libertyville, IL,) or exocad (exocad GmbH, Darmstadt, Germany) can be used for the merging step of (d). The merging function can in some embodiments combine data from separate radiographic or digital images to overlay them. This allows the user to fully utilize all data contained within a patient's images to develop treatment plans, prostheses, and appliances.

In some embodiments of the planning method, the method further includes: (e) digitally designing the dental procedure and a surgical guide; or having the dental procedure and surgical guide digitally designed by the surgeon, by a lab, or by a third party. In some embodiments, the method further includes: (f) fabricating the surgical guide; or having the surgical guide fabricated.

In some embodiments of the planning method, the method further includes: (g) performing the surgical procedure using the surgical guide.

In some embodiments, (a)-(c) are performed at the patient's first appointment for the dental procedure. In some embodiments, (a)-(c) are performed at a dental office. In some embodiments, (a)-(c) are performed at a dental office, at the patient's first appointment for the dental procedure.

In some embodiments, (d)-(f) are performed at a dental office. In other embodiments, (d)-(f) are performed at a laboratory.

In some embodiments, the digital three-dimensional radiographic image of the patient's mouth and the digital three-dimensional radiographic image of the dental model are computed tomography (CT) scans or cone beam computed tomography (CBCT) scans.

As shown in FIG. 3, at the first appointment, the dentist can use a device according to an embodiment of the subject invention to capture the occlusal registration of the patient along with the normal impressions and implant evaluation. The radiographic scan (e.g., CBCT scan) of the patient can be made at this appointment with a device according to an embodiment of the subject invention in place. After the appointment, the dentist and dental lab technician can fabricate the dental model from the impression and take the radiographic scan of the dental model with a device according to an embodiment of the subject invention in place. The result is the two required radiographic images ready for implant planning from a single appointment with radiographic markers displayed in the precise same location adjacent to the occlusal plane.

In the laboratory, the technician or dentist can use the radiographic markers, also known as fiducial markers, which are present on both images to precisely align (e.g., merge) the image of the study cast and the CBCT image of the patient using implant planning software. The result is a highly accurate model image from which a surgical guide for implant placement can be built.

The benefits of using a novel device according to the subject invention over related planning methods are numerous. The patient is required to attend one fewer appointment(s) (e.g., one appointment instead of two appointments) to receive their implant. The dentist consolidates several procedures into a single appointment and saves valuable clinic time. A traditional radiographic guide does not have to be made. The traditional radiographic guide is far more expensive and time consuming to fabricate than devices according to embodiments of the subject invention. The laboratory can devote additional time to implant planning and reduce time spent creating radiographic guides. With a standardized guide, greater accuracy during planning be achieved.

Typically, the patient will be a human; however, the device and methods can be used for dental procedures in animals as well, such as dogs and cats.

Embodiments of the subject invention can provide a constellation of asymmetric markers. This can include fiducial markers in different planes or asymmetrically positioned within, on, or outside of the device In certain embodiments one or multiple sides of device (e.g., maxillary or mandibular) can be thicker and contain the markers so they are not all in the same plane. This allows more accurate marker identification and allows the markers to be further from the teeth. In this embodiment, the main biting surface on the device can be the one of the arch being planned upon. The other arch can have a biting surface or use cotton rolls or other spacers to further distance the arches to avoid impinging on the markers.

Embodiments shown in FIGS. 8A-9B are non-limiting representations only and do not restrict the possible orientations of the markers according to the subject invention.

Embodiments can provide a combination of a shape of known dimension (SKD) and radiographic fiducial markers. This allows dental procedure planning software to relate the digital image of the patients obtained with the digital scanner to be seamlessly merged with the image obtained from the CBCT of the patient.

Embodiments comprise a shape of known dimension which could be any computer-recognizable geometric shape (2-d or 3-d) combined with a computer-recognizable pattern on its surface. The geometric shape (body of SKD) can advantageously be radiolucent so as not to interfere with imaging of fiducial marker. On the surface or inside of the SKD can be provided one or more radiopaque fiducial marker(s) in a fixed location. The fiducial marker can be located on or in the SKD in a distinct location (e.g., off-center, along one edge, or at a corner of the SKD) advantageously allowing multiple SKDs to be oriented differently to make the markers present in different planes, thus allowing better triangulation of the marker. In certain embodiments surface location of the fiducial marker provides easier manufacturing, visualization, and manipulation of the marker. This SKD/marker combination can be placed on the surface of an existing device, advantageously allowing the SKD to be able to be read by an optical or digital scanner. In alternative embodiments, markers can be provided on the interior of the SKD for scanning by a different modality besides tomography or optical scanning, either as currently practiced or as may be developed. A digital scan can register the SKD and software can be used to identify the precise location of the marker because of its distinct location and fixed spatial relation to the SKD. The marker can be embedded in the surface of the device or outside the dimensions of the body of the device. There can be provided a plurality of markers or a singular marker. The benefit of a plurality of markers can include better triangulation of the marker by the software. The benefit of a singular marker would be reduced size, cost, and complexity in operation. Embodiments can provide a marker in the shape of a sphere having benefits of being easier to manufacture and easier to locate via CBCT as compared to a more angular (non-spherical) shape of marker. Alternative embodiments can provide an angular, sharp edged, polygonal, cylindrical, or flat sheet form of a marker having benefits of ease of manufacture and handling, as well as ease of recognizing a more unique geometry in an image or a scan.

The shape of known dimension can be provided in any practical shape and could be 2-dimensional (2-d) or 3-dimensional (3-d). Embodiments can provide a SKD which is rectangular and flush with the surface of the device. Rectangular has benefits of ease of manufacturing and ability to ensure fit on the device. Flush with the surface (either 3-d or 2-d) for comfort to the patient. The marker should be positioned to not be able to move and be rigid to stay in a fixed location relative to the SKD In use, an SKD with marker can be fixed to or manufactured within the device. The SKD/marker can be removable from the device and repositionable if necessary for positioning or patient comfort. During use, the SKD is intended to be fixed in place so that the spatial relationship of the markers can be maintained among the two images for the to improve precision. An SKD in accordance with the subject invention can be designed, produced, sold, or distributed as a product independent of the device because the SKD can function independently and can be used in other applications where digital and radiographic images are to be compared or merged. By way of a non-limiting example, an SKD can also be fixed to a dental impression tray, impression material, or any other material that can obtain an occlusal registration. The SKD or marker in accordance with the subject invention can also be used in conventional radiographic scan appliances and surgical guides by fixing the SKD in or on the material during fabrication.

In certain embodiments, an SKD can have a radiolucent body with one or more radiopaque markers including letters, number, or other characters, geometric shapes, or features such as a sphere, a cone, a cylinder, or a straight line. The radiopaque markers can advantageously be located on a single face, multiple faces, contiguous faces, non-contiguous faces, or opposite faces of the base to better support the desired digital, visual, or other scanning objectives.

In some embodiments, SKDs can be provided having a diameter, width, height, length, thickness, or other useful largest, average, median, nominal, or smallest dimension of 0.1 mm, 0.5 mm, 1 mm, 1.5 mm, 2 mm, 2.5 mm, 3 mm, 4 mm, 5 mm, or more than 5 mm, including ranges, increments, divisions, combinations, and multiples thereof, as determined by the available imaging technology, needs of the patient, and needs of the dentist. In an exemplary and non-limiting embodiment, an SKD is provided having a rectangular radiolucent body with a width of 3 mm, a height of 2 mm, and a length of 5 mm, and further having a first set of radiopaque markings including letters, numbers, or recognizable geometric features on at least one side of the base that are less than 2 mm tall or less than 2 mm wide and less than 0.5 mm thick. Embodiments can further include a recognizable radiopaque fiducial marker such as a sphere on an opposite face, on a non-adjacent face, or on an adjacent face with respect to the first set of radiopaque markings.

Embodiments can provide a device with increased buffer space for teeth, whereby one or both arches of a patient can be more easily and accurately registered by the device. The addition of additional buffer space between markers and between exterior surfaces of the device can advantageously ensure reduced overlap or no overlap of teeth and markers occurs in one or more imaging approaches, thus providing a clearer and more accurate image. Increased buffer space for teeth can also be provided with a cotton spacer or other device known in the art to reliably, selectably, and cost-efficiently introduce additional spacing between an arch and the device. An increased buffer space can comprise radiolucent base material of 1 mm, 1.5 mm, 2 mm, 2.5 mm, 3 mm, 4 mm, 5 mm, 6 mm, 8 mm, 10 mm, or more than 10 mm, or 1×, 1.5×, 2×, 2.5×, 3×, 4×, 5×, 6×, 8×, 10×, or more than 10× the nominal, average, minimum, or maximum diameter, thickness, or height of the fiducial markers, including ranges, increments, divisions, combinations, and multiples thereof, as determined by the available imaging technology, needs of the patient, and needs of the dentist. In an embodiment, a device having increased buffer space for teeth according the subject invention can be provided having 3 mm diameter radiopaque fiducial markers embedded within 9 mm thick radiolucent base material, thus providing a 3× ratio of marker diameter to base material thickness.

Embodiments can provide a constellation of fiducial markers occupying multiple planes to improve triangulation of markers by software. Additionally, markers can advantageously be asymmetrical with respect to one or more planes (e.g., with respect to an anterior-posterior, medial-lateral, or inferior-superior, or other defined plane of symmetry) to improve distinctness between markers and reduce overlap during imaging or merging. In certain embodiments, asymmetric arrangement of markers is currently preferred, because of these benefits. In alternative current embodiments, or with future improvements in imaging or analysis technology (e.g., better methods to allow recognition of same plane/symmetric placements) symmetrical arrangements can provide benefits such as reduced manufacturing complexity and cost.

In an embodiment, a device according to the subject invention can provide a set of at least 5 radiopaque fiducial markers configured such that no two markers (alternatively, not more than two markers, not more than three markers, or not more than four markers) are located in any single plane nor are symmetric about any single plane in any of the anterior-posterior, medial-lateral, or superior-inferior directions. Alternatively, a device according to the subject invention can provide a set of at least 3 radiopaque fiducial markers configured such that no two markers (alternatively, not more than two markers) are located in any single plane nor are symmetric about any single plane in any of the anterior-posterior, medial-lateral, or superior-inferior directions.

In another embodiment, a device according to the subject invention can provide a set of at least 5 radiopaque fiducial markers configured such that no four markers (alternatively, not more than four markers) are located in any single plane passing through the device in any direction. In another embodiment, a device according to the subject invention can provide a set of at least 5 radiopaque fiducial markers configured such that no two pairs of markers are symmetric about any single plane passing through the device in any direction.

In certain embodiments, more than three or more than five markers, including fiducial markers and SKD markers, are provided. Six or more markers can be provided, optionally seven, eight, nine, ten, more than ten, or more than 20 markers, including ranges, increments, divisions, combinations, and multiples thereof, as determined by the available imaging technology, needs of the patient, and needs of the dentist. Embodiments with a limited number of markers (e.g., 3, 4, or 5 markers) can have advantages including reduced cost and complexity, ease of manufacture, and clear line of sight for visualizing each marker in a radiograph or other view. Embodiments with a larger number of markers (e.g., 6, 8, 12, or more markers) can have advantages including enhanced resolution, extra data points for error correction or analysis, and greater flexibility.

Figure 11A:
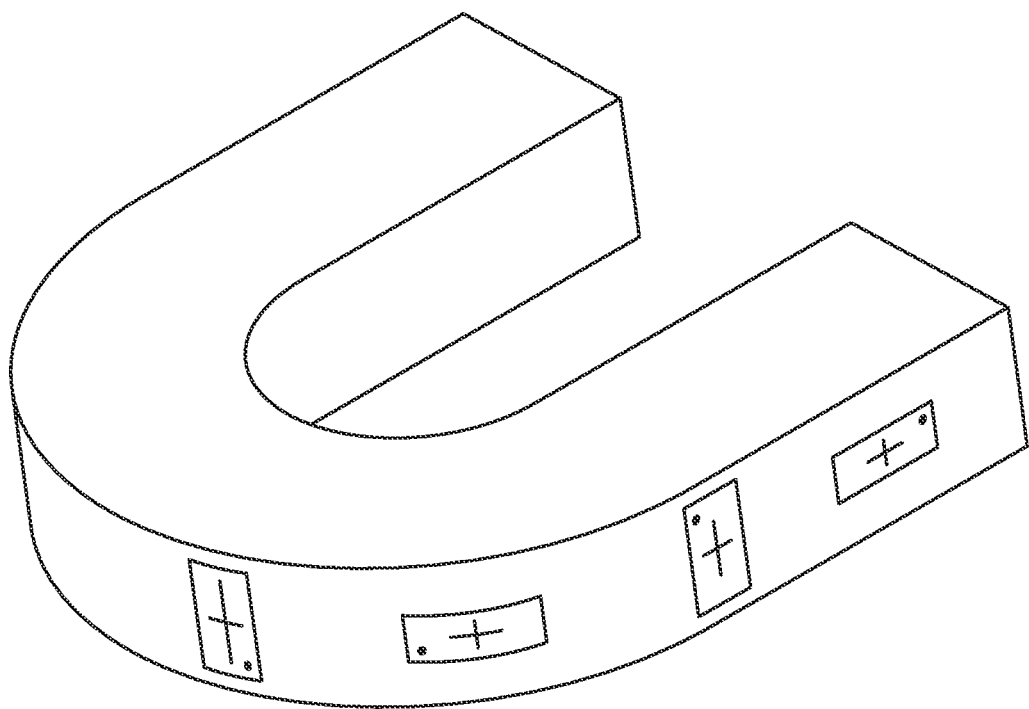
FIG. 11A shows a top perspective view of a device according to an embodiment of the subject invention comprising a radiolucent base in a U or horseshoe shape with a multiplicity of SKD markers embedded in an outer surface. In this embodiment, each marker shows a plus or cross symbol with a dot printed in the upper right corner on a first side, and a radiopaque fiducial marker affixed to the marker in the upper left corner on a second side (not visible in this perspective view) such that the dot on the first side aligns with the marker on the second side. SKD markers can be embedded within, adhered to a surface of, or otherwise attached to a device. SKD markers can conform to a surface in one or more directions, or can be rigid and maintain confirmation in one or more directions.
Figure 11B:
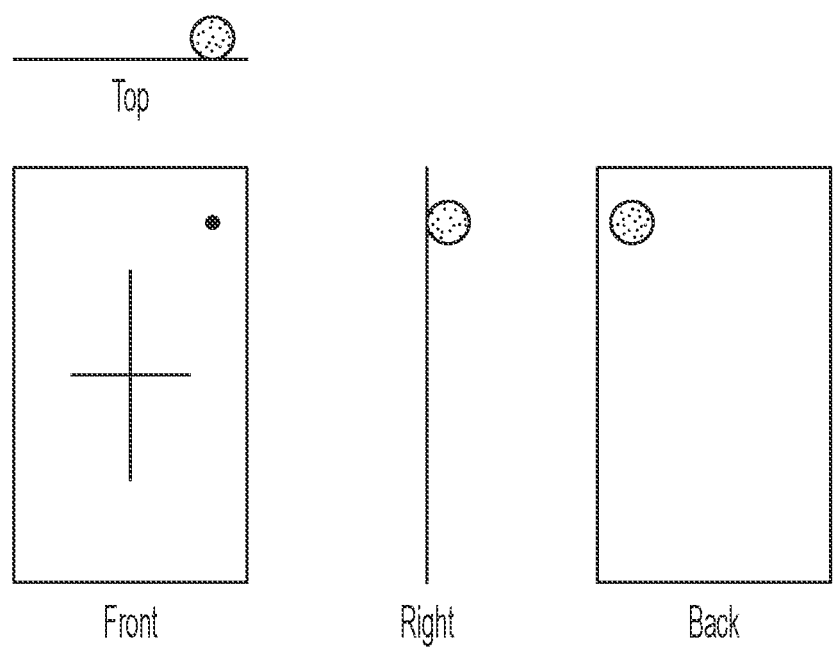
FIG. 11B shows front, right, back, and top views of an SKD marker according to an embodiment of the subject invention configured to be embedded in an outer surface of, affixed on, or embedded within a device according to an embodiment of the subject invention. In this embodiment, each marker shows a plus or cross symbol with a dot printed in the upper right corner on a first (e.g., front) side, and a radiopaque fiducial marker affixed to the marker in the upper left corner on a second (e.g., back) side such that the dot on the first side aligns with the radiopaque fiducial marker on the second side. The radiopaque fiducial marker is not visible in the front view, as it is hidden behind the body of the SKD marker. The radiopaque fiducial marker is not visible in the front view, as it is hidden behind the body of the SKD marker. The printed plus or cross symbol and dot are not visible in the back view, as they are hidden behind the body of the SKD marker. The printed plus or cross symbol and dot are not visible in the top or right views, as they can be printed flush with or debossed within the SKD marker surface. Alternative embodiments can provide visible or scannable markings (e.g., markings which are printed, etched, cut, embossed, debossed, stamped, inlaid, adhered, die cut, or by numerous other methods known in the art) which are visible or not visible in individual views and wherein features can be aligned totally or partially with other features or with one or more fiducial markers in one or more dimensions. As a non-limiting example, visible markers can be printed with a flat-lying ink or overlaid with a clear coat or sealant and can appear on the same side or opposite a fiducial or other radiopaque marker. Additionally, visible markers can be radiopaque or radiolucent, and can be visible under specified conditions (e.g., phosphorescent, infrared, or ultraviolet.)
Figure 12A:
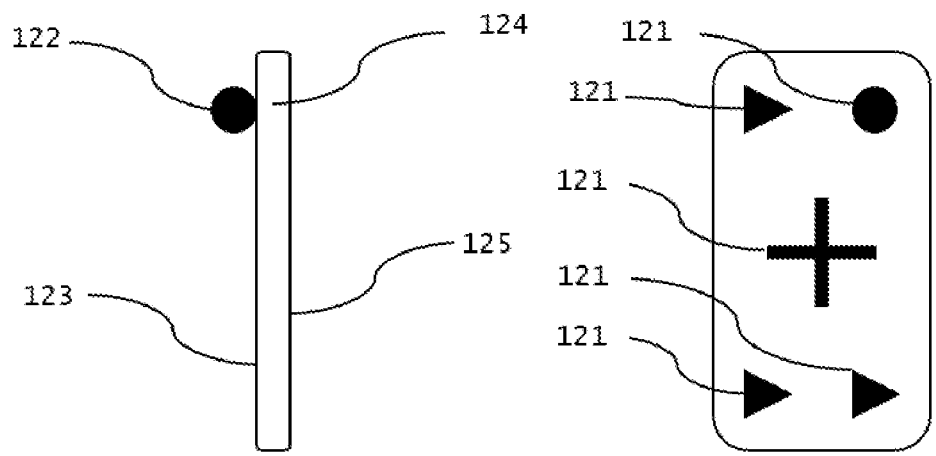
FIG. 12A shows a plan view and an edge view of an SKD marker suitable for use with a device according to an embodiment of the subject invention comprising several individual shapes of known dimension (121), a radiopaque fiducial marker (122), an interior surface for facing the device (123), a body (124), and an exterior surface for facing the patient (125). In this embodiment, the SKD marker shows a plus or cross symbol with one dot and three triangles printed on a first side, and a radiopaque fiducial marker affixed to the marker in the upper left corner on a second side such that the dot on the first side aligns with the marker on the second side. In this embodiment, the fiducial marker (122) is depicted mounted, adhered, or otherwise fastened to interior surface (123). It is noted that fiducial marker (122) can in certain embodiments be provided within or under interior surface (123), within body (124), on exterior surface (125), within or under exterior surface (125), or on or in another component, element, or layer (e.g., a component, element, or layer not depicted in this figure). It is also contemplated within the subject invention that fiducial marker (122) can have other shapes beyond that of a sphere as shown, and can include mounting, spacing, attachment, or alignment features which can interface with features or elements of the device or of the SKD marker.
Figure 12B:
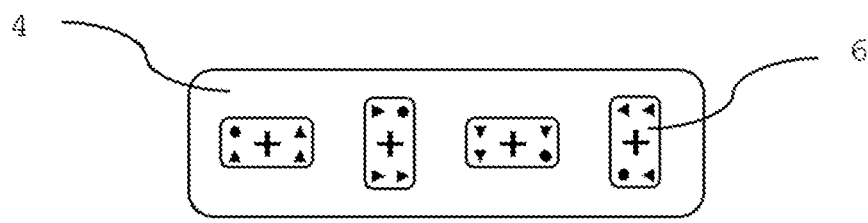
FIG. 12B shows a side view of four SKD markers according to an embodiment of the subject invention configured as embedded in an outer surface of, affixed on, or embedded within a device according to an embodiment of the subject invention. In this embodiment, each SKD marker shows a plus or cross symbol with one dot and three triangles printed on a first side, and a radiopaque fiducial marker affixed to the SKD marker in the upper left corner on a second side such that the dot on the first side aligns with the fiducial marker on the second side.

Embodiments can provide a device having markers comprising at least one off-center radiopaque fiducial marker affixed to an SKD marker comprising a visual marker symbol or pattern, letter, number, or geometric shape which can be camera or scanner readable and which can further comprise a radiopaque marker symbol or pattern, letter, number, or geometric shape on a radiolucent backer. In certain embodiments one or more SKD markers can be embedded into or adhered onto an exterior surface of the device and can be thin or flat, for instance in the form of a sticker, button, token, or label. Alternatively, the SKD marker can be thicker or three-dimensional in structure. In some embodiments one or more fiducial markers can be embedded within or adhered on the surface of the SKD marker. An embodiment can provide one or more thin radiolucent markers in the form of a label with a visible and radiopaque SKD symbol printed on a first side and a spherical, cylindrical, or flat radiopaque fiducial marker adhered to, laminated on, or embedded in an off-center position (e.g., in one corner) on a second side, as shown by way of a non-limiting example in FIGS. 11A-11B.

Alternative embodiments can provide a radiopaque fiducial marker that can be embedded such that (or the thickness and composition of the SKD marker material can be such that) the fiducial marker is visible on both sides, or is embedded completely within the SKD marker and the location of the fiducial marker indicated with one or more visible or scanner readable indicators (e.g., a printed dot, circle, or cross; a notch, slit, opening, tab, or protrusion; or a region of color, patterning, texture, threading, or surface finish; any of which can be visible or non-visible and either radiopaque or radiolucent) on either the first side, the second side, both sides, or one or more sides or edges.

EXEMPLIFIED EMBODIMENTS

The invention may be better understood by reference to certain illustrative examples, including but not limited to the following:

Embodiment 1. A device for obtaining an occlusal registration of a patient, comprising:
a base portion comprising occlusal registration material and arranged for fitting into the mouth of a patient, wherein the base portion has opposing upper and lower contacting surfaces, one or both of which is configured to be imprinted with, and maintain an impression of, the patient's dentition in the occlusal registration material; and a plurality of radiopaque fiducial markers arranged in fixed positions within the base portion, between the upper and lower contacting surfaces, wherein the fixed positions of the radiopaque fiducial markers provide reference points to determine specific anatomical areas of dentition when the base portion is fitted into the mouth of the patient and radiographically imaged.

Embodiment 2. The device of Embodiment 1, wherein the base portion has a laminated structure with two or more adjacent layers comprising occlusal registration material, plastic, or other radiolucent material, and wherein the plurality of radiopaque fiducial markers are in fixed positions between the adjacent layers.

Embodiment 3. The device of Embodiment 1 or 2, wherein the occlusal registration material comprises occlusal wax.

Embodiment 4. The device of any preceding Embodiment, wherein the plurality of radiopaque fiducial markers comprise gutta percha, barium sulfate, silicon carbide, silicon nitride, aluminum oxide, non-eugenol temporary dental cement (e.g., TempBond NE cement), any patient-safe radiopaque material, or any combination of two or more of the foregoing.

Embodiment 5. The device of any preceding Embodiment, wherein the plurality of radiopaque fiducial markers includes at least three markers, and preferably five to seven markers.

Embodiment 6. The device of any preceding Embodiment, wherein the base portion is configured as a planar sheet, or has a generally U-shaped or horseshoe configuration.

Embodiment 7. The device of any preceding Embodiment, wherein the plurality of radiopaque fiducial markers are arranged in a constellation occupying one or more than one plane or occupying more than one plane oriented in an anterior-posterior, medial-lateral, or inferior-superior direction.

Embodiment 8. The device of any preceding Embodiment, wherein the plurality of radiopaque fiducial markers are arranged in a symmetric or asymmetric pattern with respect to an anterior-posterior, medial-lateral, or inferior-superior, or other defined plane of symmetry.

Embodiment 9. A device for obtaining an occlusal registration of a patient, comprising:

a base portion comprising occlusal registration material and arranged for fitting into the mouth of a patient, wherein the base portion has opposing upper and lower contacting surfaces, one or both of which is configured to be imprinted with, and maintain an impression of, the patient's dentition in the occlusal registration material; and a plurality of shape of known dimension (SKD) markers arranged in fixed positions within or on the base portion, wherein the fixed positions of the SKD markers provide reference points to determine specific anatomical areas of dentition when the base portion is fitted into the mouth of the patient and imaged.

Embodiment 10. The device of Embodiment 9, wherein the base portion has one or more external surfaces visible when the device is worn by the patient, and wherein the plurality of SKD markers are fixed in positions which are visible when the device is worn by the patient.

Embodiment 11. The device of Embodiment 9 or 10, wherein the occlusal registration material comprises occlusal wax.

Embodiment 12. The device of any one of Embodiments 9 to 11, wherein the plurality of SKD markers further comprise a fiducial marker comprising gutta percha, barium sulfate, silicon carbide, silicon nitride, aluminum oxide, non-eugenol temporary dental cement (e.g., TempBond NE cement), or any combination of two or more of the foregoing.

Embodiment 13. The device of any one of Embodiments 9 to 12, wherein the plurality of SKD markers includes at least three markers, and preferably five to seven markers.

Embodiment 14. The device of any one of Embodiments 9 to 13, wherein the base portion is configured as a planar sheet, or has a generally U-shaped or horseshoe configuration.

Embodiment 15. The device of any one of Embodiments 9 to 14, wherein the plurality of SKD markers are arranged in a constellation occupying one or more than one plane or occupying more than one plane oriented in an anterior-posterior, medial-lateral, or inferior-superior direction.

Embodiment 16. The device of any one of Embodiments 9 to 15, wherein the plurality of SKD markers are arranged in a symmetric or asymmetric pattern with respect to an anterior-posterior, medial-lateral, or inferior-superior, or other defined plane of symmetry.

Embodiment 17. A device for obtaining an occlusal registration of a patient, comprising:

a visible shape of known dimension (SKD) marker comprising a visual marker symbol or pattern, letter, number, or geometric shape which is camera or scanner readable and at least one off-center radiopaque fiducial marker affixed to or incorporated in the visible SKD marker.

Embodiment 18. The device of Embodiment 17, wherein the visual marker symbol or pattern, letter, number, or geometric shape further comprises a radiopaque marker symbol or pattern, letter, number, or geometric shape on a radiolucent backer.

Embodiment 19. The device of Embodiment 18, the radiopaque marker symbol or pattern, letter, number, or geometric shape on the radiolucent backer having the same appearance as the visual marker symbol or pattern, letter, number, or geometric shape.

Embodiment 20. The device of Embodiment 19, the radiopaque marker symbol or pattern, letter, number, or geometric shape on the radiolucent backer being formed together with the visual marker symbol or pattern, letter, number, or geometric shape which is camera or scanner readable.

Embodiment 21. The device of Embodiment 20, the SKD marker being embedded into or adhered onto an exterior surface of the device.

Embodiment 22. The device of Embodiment 21, the SKD marker being thin or flat, in the form of a sticker, button, token, or label.

Embodiment 23. The device of Embodiment 21, the SKD marker having a thickness, a width, and a height; and the thickness being at least one quarter of either the width or the height, such that the SKD marker is three-dimensional in structure.

Embodiment 24. The device of Embodiment 21, the at least one off-center radiopaque fiducial marker being embedded within or adhered on the surface of the SKD marker.

Embodiment 25. A device for obtaining an occlusal registration of a patient, comprising:

one or more thin radiolucent markers in the form of a label with a first visible SKD symbol printed on a first side of the label and a spherical, cylindrical, or flat radiopaque fiducial marker adhered to, laminated on, or embedded on a second side of the label.

Embodiment 26. The device of Embodiment 25, the radiopaque fiducial marker on the second side of the label aligned with the visible SKD symbol printed on the first side of the label, such that a visible scan and a radiographic scan can be at least partially aligned by location of the fiducial marker in the radiographic scan with respect to the visible SKD symbol in the visible scan.

Embodiment 27. A method for obtaining an occlusal registration of a patient, comprising placing the device of any one of Embodiments 1 to 26 into the mouth of a patient, wherein the patient's occlusal registration is obtained when the patient bites on the upper and lower contacting surfaces, making an impression of the patient's dentition in the occlusal registration material.

Embodiment 28. A method for dental procedure planning, comprising:

(a) obtaining an occlusal registration of a patient comprising placing the device of any one of Embodiments 1 to 26 into the mouth of a patient, wherein the patient's occlusal registration is obtained when the patient bites on the upper, lower, or both contacting surfaces, making an impression of the patient's dentition in the occlusal registration material; and (b) obtaining a digital three-dimensional radiographic or visual image of the patient's mouth with the device placed in the patient's mouth.

The method of Embodiment 28, further comprising: (c) obtaining a digital three-dimensional radiographic or visual image of a dental model of the patient with the device placed on the model.

Embodiment 30. The method of Embodiment 29, further comprising: (d) merging the radiographic or visual image of the patient's mouth and the radiographic or visual image of the dental model utilizing the radiopaque fiducial markers or SKD markers or both; or providing the radiographic or visual image of the patient's mouth and a CBCT scan of the dental model to a laboratory to perform the merging.

Embodiment 31. The method of Embodiment 30, further comprising: (e) digitally designing the dental procedure and a surgical guide; or having the dental procedure and surgical guide digitally designed.

Embodiment 32. The method of Embodiment 31, further comprising: (f) fabricating the surgical guide; or having the surgical guide fabricated.

Embodiment 33. The method of Embodiment 32, further comprising: (g) performing the surgical procedure using the surgical guide.

Embodiment 34. The method of any preceding Embodiment, further comprising assessing the patient's complaint, medical history and dental history prior to said obtaining the occlusal registration of the patient of (a).

Embodiment 35. The method of any one of Embodiments 29 to 34, wherein (a)-(c) are performed at the patient's first appointment for the dental procedure.

Embodiment 36. The method of any one of Embodiments 29 to 34, wherein (a)-(c) are performed at a dental office.

Embodiment 37. The method of any one of Embodiments 29 to 34, wherein (a)-(c) are performed at a dental office at the patient's first appointment for the dental procedure.

Embodiment 38. The method of Embodiment 32, wherein (d)-(f) are performed at a dental office.

Embodiment 39. The method of Embodiment 32, wherein (d)-(f) are performed at a laboratory.

Embodiment 40. The method of any preceding Embodiment, wherein the dental procedure is a dental implant procedure.

Embodiment 41. The method of any preceding Embodiment, wherein the digital three-dimensional radiographic or visual image of the patient's mouth and the digital three-dimensional radiographic or visual image of the dental model are computed tomography (CT) scans or cone beam computed tomography (CBCT) scans.

EXAMPLES

Prophetic Example 1: Prophetic description of the creation of a surgical guide in the laboratory in accordance with embodiments of the subject invention.

Figure 4:
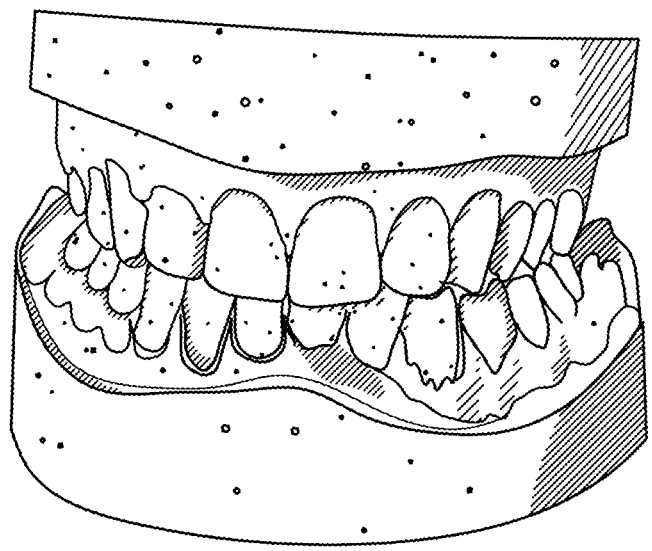
FIG. 4 shows a dental study model, which is a three-dimensional replica of the patient's oral anatomy (e.g., size and relationship of the teeth, gums, and optionally dental arch) and can be used in accordance with the subject invention.

A dental study model, which is a three-dimensional replica of the patient's oral anatomy (e.g., size and relationship of the teeth, gums, and optionally dental arch) can be created in a lab simulation of a single dental care appointment, for use in accordance with the subject invention, as depicted in FIG. 4.

Figure 5:
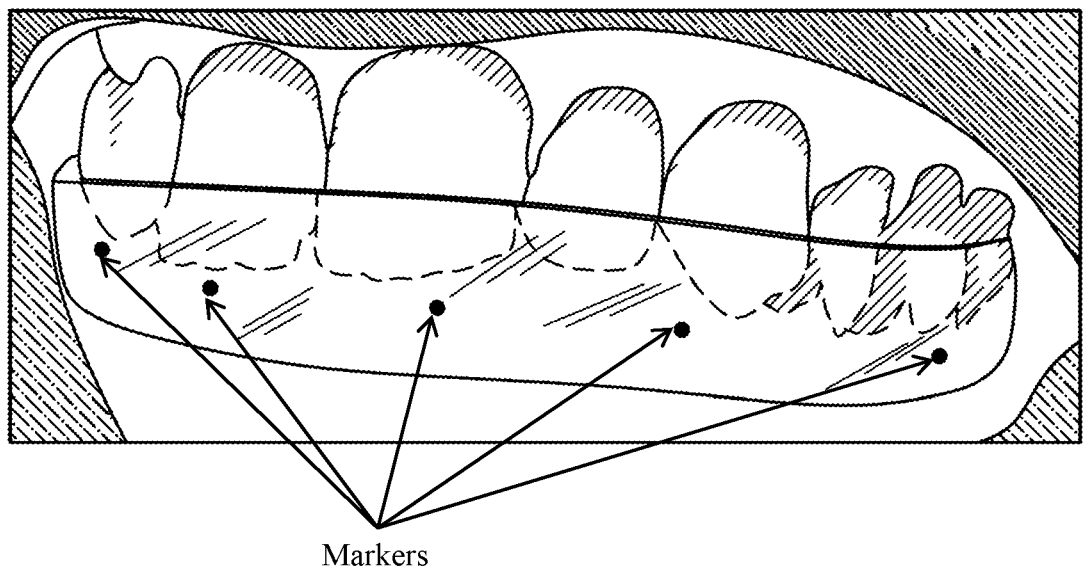
FIG. 5 shows a device according to an embodiment of the subject invention placed in the patient's mouth so that a CBCT scan can be made of the patient's dentition. The fiducial markers are indicated.

A device according to an embodiment of the subject invention can be placed in the patient's mouth and a CBCT scan made of the patient's dentition with the device in place during the same lab simulation of a single dental care appointment. The fiducial markers can be placed in the device and indicated with additional visual markings in the form of orange dots, as depicted (with black dots) in FIG. 5.

Figure 6:
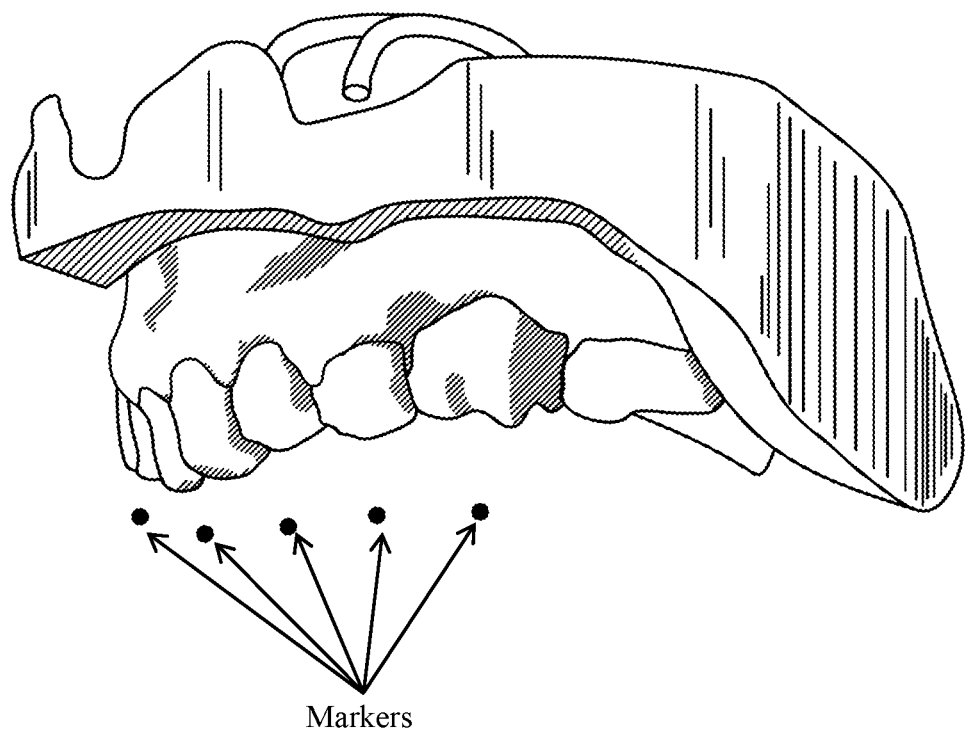
FIG. 6 depicts a CBCT image of the side of the study model of FIG. 4, with a device according to an embodiment of the subject invention fitted thereon. The fiducial markers are shown in the CBCT image of the study model, corresponding to precisely where they were in the patient's mouth in FIG. 5.

A CBCT image can be taken of the study model of FIG. 4, with the device according to an embodiment of the subject invention fitted thereon. The digital representation of the fiducial markers can be visible in the CBCT image of the study model, corresponding to precisely where they were in the patient's mouth in FIG. 5. The digital superposition of the markers from the CBCT scan of the patient's mouth and the CBCT scan of the dental study model can allow for precise alignment of the two digital images in three dimensions, as depicted in FIG. 6.

Figure 7:
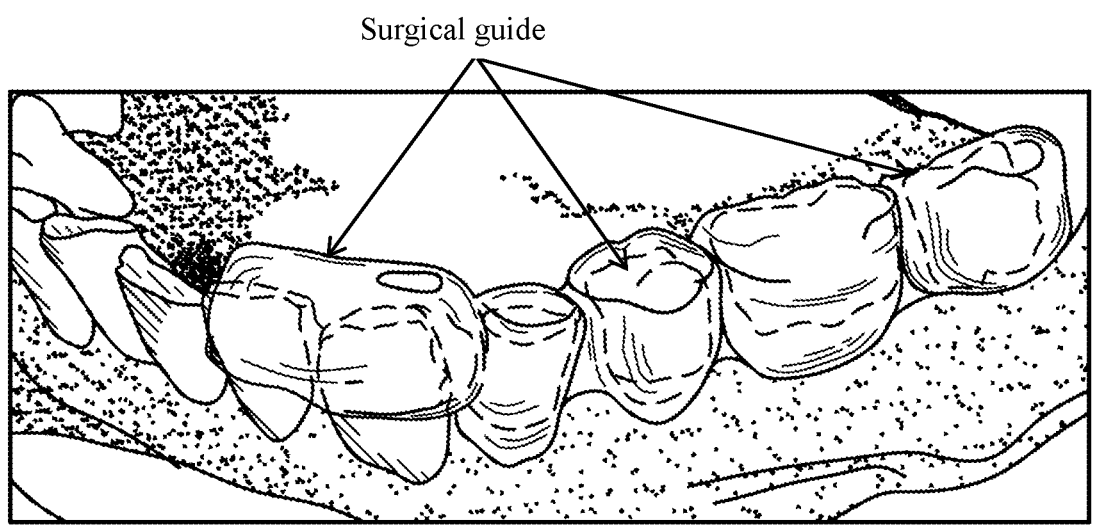
FIG. 7 depicts a surgical guide placed on a patient's lower jaw, allowing the dentist to place the dental plant with a high degree of accuracy. The surgical guide shown can be created after only one patient appointment using device(s) and method(s) in accordance with embodiments of the subject invention, an advantageous improvement over related art devices and methods, requiring two appointments and fabrication of an intermediate scan appliance.
Figure 8A:
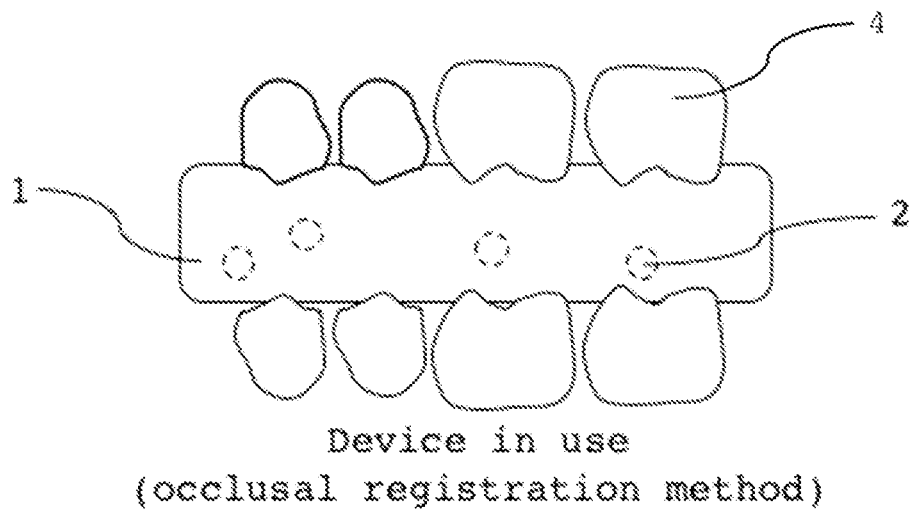
FIG. 8A shows a side view of a device according to an embodiment of the subject invention placed in the patient's mouth so that a depression model of patient's dentition (4) can be made using an occlusal or other registration method. The radiopaque fiducial markers (2) of this embodiment are indicated as dashed circles to reflect their position within the occlusal registration material (1) of the base. The embodiment depicted in FIG. 8A is similar to the embodiment depicted in the upper panel of FIG. 1J but with a different number of fiducial markers arranged in a different constellation pattern.
Figure 8B:
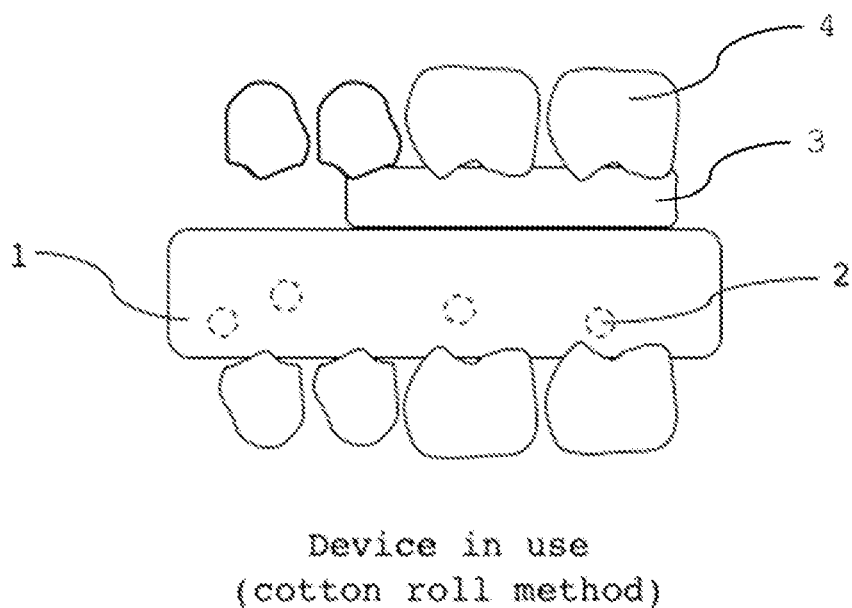
FIG. 8B shows a side view of a device according to an embodiment of the subject invention placed in the patient's mouth so that a depression model of patient's dentition (4) can be made using a spacer method with cotton roll (3) or other spacer. The radiopaque fiducial markers (2) of this embodiment are indicated as dashed circles to reflect their position within the occlusal registration material (1) of the base. The embodiment depicted in FIG. 8B is similar to the embodiment depicted in the lower panel of FIG. 1J but with a different number of fiducial markers arranged in a different constellation pattern.
Figure 9A:
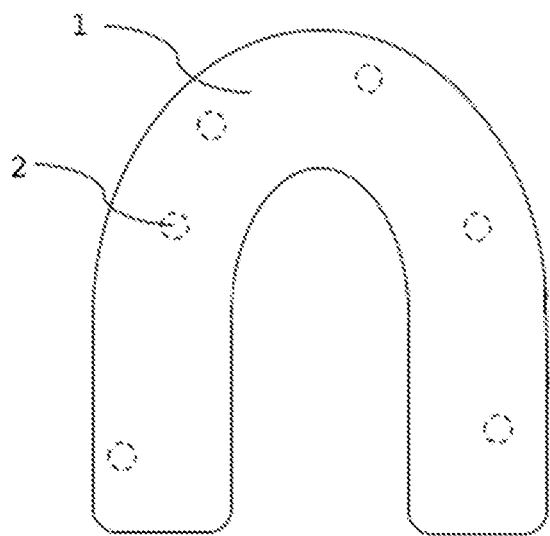
FIG. 9A shows a top view of a U or horseshoe shaped device according to an embodiment of the subject invention for taking a depression model of patient's dentition (not shown in this figure). The radiopaque fiducial markers (2) of this embodiment are indicated as dashed circles to reflect their position within the occlusal registration material (1) of the base. The embodiment depicted in FIG. 9A is similar to the embodiments depicted in FIGS. 1A-1D but with a different number of fiducial markers arranged in a different constellation pattern and a different width and thickness of occlusal registration material.
Figure 9B:
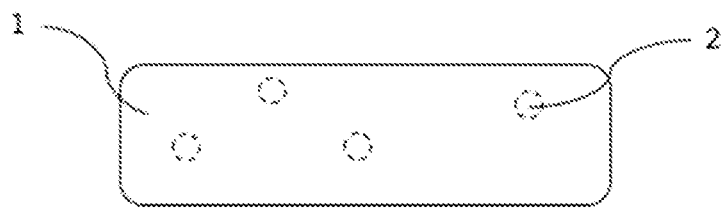
FIG. 9B shows a side view of a U or horseshoe shaped device according to an embodiment of the subject invention for taking a depression model of patient's dentition (not shown in this figure). The radiopaque fiducial markers (2) of this embodiment are indicated as dashed circles to reflect their position within the occlusal registration material (1) of the base. The embodiment depicted in FIG. 9B is similar to the embodiments depicted in FIGS. 1A-1D but with a different number of fiducial markers arranged in a different constellation pattern and a different width and thickness of occlusal registration material.
Figure 10A:
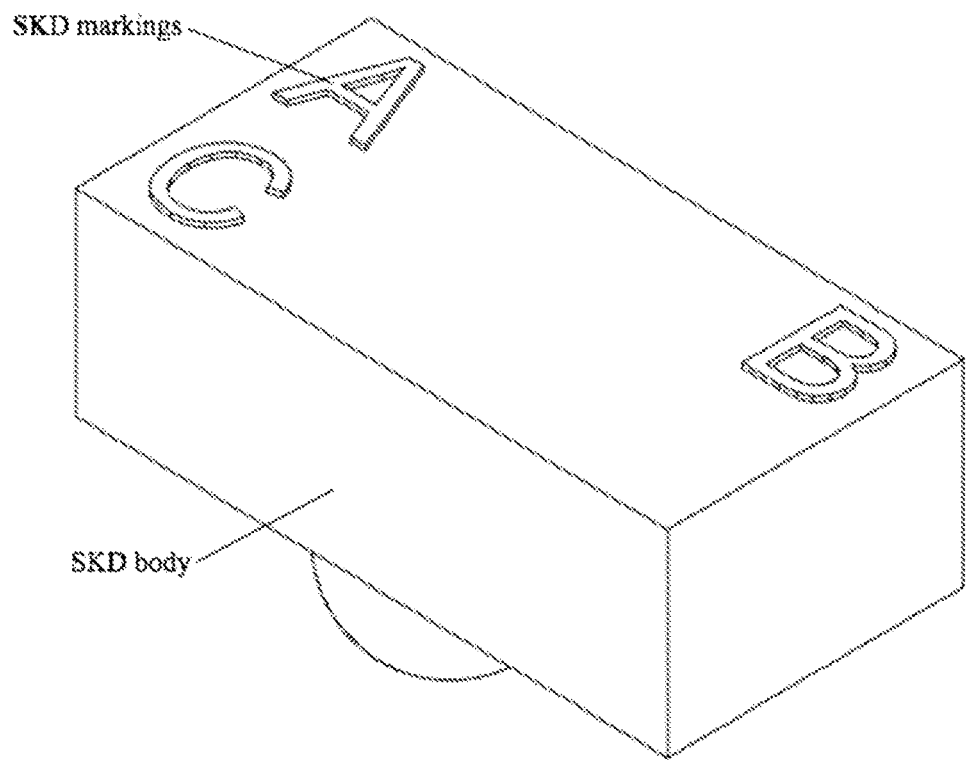
FIG. 10A shows a top perspective view of a shape of known dimension, an SKD, according to an embodiment of the subject invention comprising a rectangular body which can be radio lucent, shape of known dimension (SKD) markings (block letters on the top surface in this embodiment) which can be radiopaque, and a radiopaque fiducial marker (a sphere on the bottom surface in this embodiment, partially visible beneath the rectangular body).
Figure 10B:
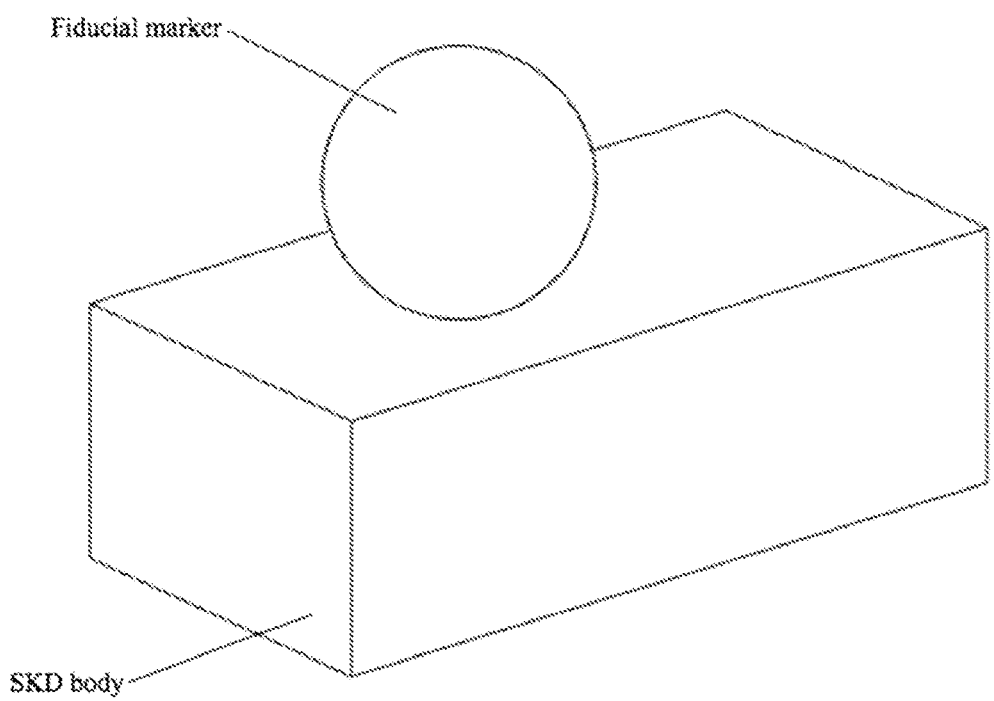
FIG. 10B shows a bottom perspective view of an SKD according to an embodiment of the subject invention comprising a rectangular body which can be radio lucent, SKD markings (block letters on the top surface in this embodiment, not visible in this view) which can be radiopaque, and a radiopaque fiducial marker (a sphere on the bottom surface in this embodiment, fully visible in this view).

A surgical guide can be created in accordance with the subject invention for placement on a patient's lower jaw, simulating allowing the dentist to place the dental implant with a high degree of accuracy. The surgical guide shown (as depicted in FIG. 7) can be created after only one simulated patient appointment using devices and methods in accordance with embodiments of the subject invention, an advantageous improvement over related art devices and methods requiring two appointments.

Actual Example 2: Description of manufacture and use of digital registration device with SKD markers in accordance with the subject invention.

A dental study model, which is a three-dimensional replica of the patient's oral anatomy (e.g., size and relationship of the teeth, gums, and optionally dental arch) was created from images captured with a digital scanning device (eg OmniCam) with an enhanced dental registration device according to an embodiment of the invention, including SKD markers, fitted to the patient's teeth as previously described. Images that included the device and the affixed SKDs were collected.

A CBCT image was obtained of the patient while wearing the device as previously described.

The digital imagery of the optical scan of the patient's dentition captured the SKD, which allowed merging software to have precision 3-dimensional locations of the fiducial markers due to the fixed relative locations of the fiducial markers from the SKDs. The digital superposition of the markers from the CBCT scan of the patient's mouth allowed for precise alignment of the two digital images in three dimensions, as depicted in FIG. 6.

A surgical guide was created in accordance with the subject invention for placement on a patient's lower jaw, simulating allowing the dentist to place the dental implant with a high degree of accuracy. The surgical guide shown (as depicted in FIG. 7) was created after only one simulated patient appointment using devices and methods in accordance with embodiments of the subject invention, an advantageous improvement over related are devices and methods requiring two appointments.

Prophetic Example 3: Prophetic description of manufacture and use of SKD markers as a standalone component for constructing a digital registration device or other device in accordance with the subject invention.

A dental laboratory has an order to plan implant placement for a patient. The provider sent a physical diagnostic cast of the patient's dentition. The dental laboratory used a plastic matrix (or acrylic or another similar material) to form the body of a scan appliance. The SKD markers were then fixed to the body of the scan appliance. The scan appliance was returned to the provider. The provider has the ability to capture an image of the patient using CBCT imaging or via optical scanning. From there, the provider can continue to plan the implant. In this method, the laboratory fabricates a scan appliance. While this does not save an appointment, it reduces dentist working chairside and allows for digital scanning if the dentist did not have that capability previously. There are also special clinical instances where a laboratory fabricated scan appliance can be preferable or indicated (special medical need, unusual dentition, as required by the procedure, etc.)

Prophetic Example 4: Prophetic description of a dentist custom making a scan appliance with SKD markers according to an embodiment of the subject invention.

The dentist would take a polyvinyl siloxane impression of the patient using an impression tray. The impression tray would be modified to allow the SKD markers to be fixed to the impression tray (e.g., drill away material from the impression tray and fix the markers with adhesive). The patient would have a CBCT image taken of them with the device fitted properly. A physical cast would be made and then the tray would be fitted to the cast. A CBCT of the cast with custom scan appliance would be made. An optical scan is unlikely in this case because of the bulk of the impression and tray. Advantages include better markers, typically, in related art, they would be hand spun balls of gutta percha, hardly precise and subject to variability. This also saves an appointment and enables the dentist to capture a physical impression of the patient.

Alternatively, the dentist could take a piece of occlusal wax, have the patient register their teeth on it, then fix the SKD markers to the wax. Then optically scan the patient with the device fitted (capturing the SKDs) and CBCT the patient with the device fitted. This gives the two necessary images for the surgical guide to be created. This allows the provider to optically scan the patient with a custom device and save one appointment.

Definitions

As used herein, the terms "a," "an," "the" and similar terms used in the context of the present invention (especially in the context of the claims) are to be construed to cover both the singular and plural unless otherwise indicated herein or clearly contradicted by the context. Thus, for example, reference to "a marker" or "an image" should be construed to cover both a singular marker or singular image and a plurality of markers and a plurality of images unless indicated otherwise or clearly contradicted by the context.

As used herein, the term "dental procedure planning" broadly refers to any step, subset of steps, or all steps, in the dental procedure planning process, from assessing the patient's complaint, medical history, and dental history, to completion of the dental procedure, or any point or points there between.

As used herein, the terms "study model", "study cast", and "diagnostic cast" are used interchangeably to refer to the positive reproduction of a patient's teeth and associated soft tissue made from a dental impression obtained from the patient either physically or digitally, and is a type of dental model and is an important component in dental implant planning. The study model is a physical (typically, stone) or digital replica of the patient's hard and soft tissues that allows study of the dentition outside the patient's mouth. It is a highly accurate model that can be used to fabricate dental appliances. In conventional dental procedure planning (e.g., conventional dental implant planning), the study model is used to make a radiographic guide and a surgical guide.

As used herein, the terms "registration" and "dental registration" are used interchangeably to refer to occlusal registrations, registration of the teeth of one arch, or registration of a subset of teeth in the mouth of a patient.

As used herein, the terms "patient" and "subject" are used interchangeably herein to refer to a human or non-human animal. Thus, the device and methods of the invention are useful for veterinary patients, including domesticated animals such as dogs and cats.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:

1. A device for obtaining an occlusal registration of a patient, comprising:
one or more radiolucent markers in the form of a flat label having a first face and an opposite second face with a first visible SKD symbol printed on the first face of the flat label and a spherical, cylindrical, or flat radiopaque fiducial marker adhered to, laminated on, or embedded on the opposite second face of the flat label.

2. The device of claim 1, wherein the radiopaque fiducial marker on the opposite second face of the flat label is aligned with the visible SKD symbol printed on the first face of the flat label, such that a visible scan and a radiographic scan can be at least partially aligned by location of the fiducial marker in the radiographic scan with respect to the visible SKD symbol in the visible scan.

3. The device of claim 1, further comprising an occlusal registration material configured to receive an occlusal registration of a patient.

4. A method for obtaining an occlusal registration of a patient, comprising placing the device of claim 1 into the mouth of a patient, wherein the patient's occlusal registration is obtained when the patient bites on opposing upper and lower contacting surfaces, thereby making an impression of the patient's dentition in an occlusal registration material.

5. A method for obtaining an occlusal registration of a patient, comprising placing the device of claim 2 into the mouth of a patient, wherein the patient's occlusal registration is obtained when the patient bites on opposing upper and lower contacting surfaces, thereby making an impression of the patient's dentition in an occlusal registration material.

6. A method for obtaining an occlusal registration of a patient, comprising placing the device of claim 3 into the mouth of a patient, wherein the patient's occlusal registration is obtained when the patient bites on opposing upper and lower contacting surfaces, thereby making an impression of the patient's dentition in the occlusal registration material.

* * * * *

UNITED STATES PATENT AND TRADEMARK OFFICE
CERTIFICATE OF CORRECTION

| | | |
|---|---|---|
| PATENT NO. | : 11,833,010 B2 | Page 1 of 1 |
| APPLICATION NO. | : 17/997694 | |
| DATED | : December 5, 2023 | |
| INVENTOR(S) | : Robert Kyle Koski | |

It is certified that error appears in the above-identified patent and that said Letters Patent is hereby corrected as shown below:

In the Specification

Column 19,
Line 31, "The method of Embodiment 28" should read --Embodiment 29. The method of Embodiment 28--.

Signed and Sealed this
Thirteenth Day of May, 2025

Coke Morgan Stewart
*Acting Director of the United States Patent and Trademark Office*